(12) United States Patent
Lyden et al.

(10) Patent No.: US 10,844,436 B2
(45) Date of Patent: Nov. 24, 2020

(54) USE OF DOUBLE-STRANDED DNA IN EXOSOMES: A NOVEL BIOMARKER IN CANCER DETECTION

(71) Applicants: CORNELL UNIVERSITY, Ithaca, NY (US); SLOAN-KETTERING INSTITUTE FOR CANCER RESEARCH, New York, NY (US)

(72) Inventors: David C. Lyden, New York, NY (US); Hector Peinado Selgas, New York, NY (US); Haiying Zhang, New York, NY (US); Basant Kumar Thakur, New York, NY (US); Annette Becker, New York, NY (US); Jacqueline Bromberg, West Nyack, NY (US)

(73) Assignees: CORNELL UNIVERSITY, Ithaca, NY (US); SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

(21) Appl. No.: 15/300,639

(22) PCT Filed: Apr. 1, 2015

(86) PCT No.: PCT/US2015/023832
§ 371 (c)(1),
(2) Date: Sep. 29, 2016

(87) PCT Pub. No.: WO2015/153732
PCT Pub. Date: Oct. 8, 2015

(65) Prior Publication Data
US 2017/0175200 A1 Jun. 22, 2017

Related U.S. Application Data

(60) Provisional application No. 61/973,635, filed on Apr. 1, 2014.

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/106* (2013.01); *C12Q 2600/112* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 5,849,701 | A | 12/1998 | Roberts et al. |
| 7,147,852 | B2 | 12/2006 | Gilbertson |
| 7,511,056 | B2 | 3/2009 | Dieferibacher et al. |
| 8,158,589 | B2 | 4/2012 | Dotor Herrerias et al. |
| 8,569,462 | B2 | 10/2013 | Bedinger et al. |
| 8,691,944 | B2 | 4/2014 | Clark et al. |
| 9,816,998 | B2 | 11/2017 | Lyden et al. |
| 9,921,223 | B2 * | 3/2018 | Kalluri ............. G01N 33/57488 |
| 2010/0184046 | A1 | 7/2010 | Klass et al. |
| 2010/0196426 | A1 | 8/2010 | Skog et al. |
| 2011/0118298 | A1 * | 5/2011 | Fritz ................ G01N 33/57492 514/291 |
| 2011/0160210 | A1 | 6/2011 | Fleenor et al. |
| 2012/0208706 | A1 | 8/2012 | Downing et al. |
| 2013/0005599 | A1 | 1/2013 | Klass |
| 2013/0029339 | A1 | 1/2013 | Skog et al. |
| 2013/0177498 | A1 | 7/2013 | Goldenberg et al. |
| 2013/0287801 | A1 | 10/2013 | Castronovo et al. |
| 2014/0038901 | A1 | 2/2014 | Lyden et al. |
| 2014/0045915 | A1 | 2/2014 | Skog et al. |
| 2014/0162888 | A1 | 6/2014 | Kuslich et al. |

(Continued)

FOREIGN PATENT DOCUMENTS

WO 2005/091805 6/2005
WO 2009/100029 A1 8/2009

(Continued)

OTHER PUBLICATIONS

International Search Report and Written Opinion for corresponding Application No. PCT/US2015/023832 (dated Jul. 21, 2015).
Kahlert et al., "Identification of Double-Stranded Genomic DNA Spanning Chromosomes with Mutated KRAS and p53 DNA in the Serum Exosomes of Patients with Pancreatic Cancer," J. Biol. Chem. 289(7):3869-3875 (2014).
Thakur et al., "Double-Stranded DNA in Exosomes: A Novel Biomarker in Cancer Detection," Cell Res. 24 (6):766-769 (2014).
Extended European Search Report and European search opinion for European Application No. 15774168.7 dated Oct. 27, 2017.
Partial European Search Report for corresponding European Application No. 15774168.7 dated Jan. 1, 2019.
Guescini et al., "Astrocytes and Glioblastoma Cells Release Exosomes Carrying mtDNA," J Neural Transm 117 (1):1-4 (2010).
Balaj et al., "Tumour Microvesicles Contain Retrotransposon Elements and Amplified Oncogene Sequences," Nat Commun 2:180 (2011).

(Continued)

*Primary Examiner* — Carla J Myers
(74) *Attorney, Agent, or Firm* — Troutman Pepper Hamilton Sanders LLP (Rochester)

(57) ABSTRACT

The present invention is directed to methods of prognosing, treating, or managing treatment of cancer in a subject. These methods involve selecting a subject having cancer, obtaining, from the selected subject, a sample containing exosomes, recovering the exosomes from the sample, and isolating the double-stranded DNA from within the exosomes. The isolated double-stranded DNA is then used to detect the presence or absence of one or more genetic mutations associated with cancer, quantify the amount of isolated double-stranded DNA from the recovered exosomes in the sample, detect the methylation status of the isolated double-stranded DNA, or quantify the amount isolated double-stranded DNA able to enter a recipient cell. The prognosing, treating, or managing treatment is carried out based on this information.

24 Claims, 11 Drawing Sheets

Specification includes a Sequence Listing.

(56) References Cited

U.S. PATENT DOCUMENTS

| | | |
|---|---|---|
| 2014/0227179 A1 | 8/2014 | Liu et al. |
| 2015/0218651 A1 | 8/2015 | Lyden et al. |
| 2017/0175200 A1 | 6/2017 | Lyden et al. |
| 2018/0045728 A1* | 2/2018 | Kalluri ............ G01N 33/57488 |
| 2018/0231558 A1 | 8/2018 | Lyden et al. |
| 2019/0049435 A1 | 2/2019 | Lyden et al. |

FOREIGN PATENT DOCUMENTS

| | | |
|---|---|---|
| WO | 2010/056337 A2 | 5/2010 |
| WO | 2010/141955 | 12/2010 |
| WO | 2012/031008 | 3/2012 |
| WO | 2012/135844 | 10/2012 |
| WO | 2013/028788 A1 | 2/2013 |
| WO | 2013/134786 A2 | 9/2013 |
| WO | 2014/028862 A1 | 2/2014 |
| WO | 2014/037332 | 3/2014 |
| WO | 2014/055775 A1 | 4/2014 |
| WO | 2014/062978 | 4/2014 |

OTHER PUBLICATIONS

Zhang et al., "Stimulated Human Mast Cells Secrete Mitochondrial Components That Have Autocrine and Paracrine Inflammatory Actions," PLOS ONE 7(12):1-9 (2012).

Zimmer et al., "The S100 Protein Family: History, Function, and Expression," Brain Research Bulletin 37(4):417-429 (1995).

Schmid et al., "EGFR/KRAS/BRAF Mutations in Primary Lung Adenocarcinomas and corresponding Locoregional Lymph Node Metastase," Clin Cancer Res. 15:4554 (2009).

Adamczyk et al., "Characterization of Soluble and Exosomal Forms of the EGFR Released from Pancreatic Cancer Cells," Life Sciences 89:304 (2011).

Batagov et al., "Exosomes Secreted by Human Cells Transport Largely mRNA Fragments that are Enriched in the 3'-Untranslated Regions," Biology Direct 8(12):1-8 (2013).

Fesler et al., "Circulating microRNA Testing for the Early Diagnosis and Follow-up of Colorectal Cancer Patients," Mol. Diagn. Ther. 18(3):303-308 (2014).

Mathivanan et al., "Exosomes: Extracellular Organelles Important in Intercellular Communication," J. Proteomics 73:1907-1920 (2010).

Zhang et al., "A Niche Role for Cancer Exosomes in Metastasis," Nat. Cell Biol. 17(6):709-711 (2015).

Seton-Rogers, "Metastasis: An Influential Delivery," Nat. Rev. Cancer 15(7):386 (2015).

Ferrarelli, "Exosomes Prep the Metastatic Site," Sci. Signal. 8(380):ec150 (2015).

Vignieri and Smith, "Cancer Biology: Tumor Cells Educate the Metastatic Niche," Science Magazine 348 (6240):1220 (Jun. 12, 2015).

Ray, "Pancreatic Cancer Exosomes Prime the Liver for Metastasis," Nat. Rev. Gastroenterol. Hepatol. 12(7):371 (2015).

Costa-Silva et al., "Pancreatic Cancer Exosomes Initiate Pre-Metastatic Niche Formation in the Liver," Nat. Cell Biol. 17:816-826 (2015).

Hagemann et al., "Macrophages Induce Invasiveness of Epithelial Cancer Cells via NF-kappaB and JNK," J. Immunol. 175:1197-1205 (2005).

Desgrosellier et al., "Integrins in Cancer: Biological Implications and Therapeutic Opportunities," Nat Rev Cancer 10(1):9-22 (2010).

Enns et al., "Alphavbeta5-integrins Mediate Early Steps of Metastasis Formation," Eur J Cancer 41(7)1065-1072 (2005).

Nair et al., "HYD1-induced Increase in Reactive Oxygen Species Leads to Autophagy and Necrotic Cell Death in Multiple Myeloma Cells," Mol Cancer Ther. 8(8)2441-2451 (2009).

Mullamitha et al, "Phase I Evaluation of a Fully Human Anti-Alphav Integrin Monoclonal Antibody (CNTO 95) in Patients With Advanced Solid Tumors," Clin. Cancer Res. 13(7):2128-2135 (2007).

* cited by examiner

A.

B.

A.

B.

USE OF DOUBLE-STRANDED DNA IN EXOSOMES: A NOVEL BIOMARKER IN CANCER DETECTION

This application is a national stage application under 35 U.S.C. § 371 of PCT Application No. PCT/US2015/023832, filed Apr. 1, 2015, which claims the priority benefit of U.S. Provisional Patent Application Ser. No. 61/973,635, filed Apr. 1, 2014, which is hereby incorporated by reference in its entirety.

This invention was made with government support under grant number RO1-CA169416 awarded by the National Institutes of Health and grant numbers W81XWH-13-1-0427 and W81XWH-12-BCRP-IDEA awarded by the United States Department of Defense. The government has certain rights in the invention.

FIELD OF THE INVENTION

The present invention relates to the use of double-stranded DNA in exosomes as a novel biomarker in cancer detection.

BACKGROUND OF THE INVENTION

Various cancer types have been described to release exosomes; small membrane vesicles generated either through budding off the plasma membrane or through the release by the fusion of multivesicular bodies with the plasma membrane (Peinado et al., "The Secreted Factors Responsible for Pre-metastatic Niche Formation: Old Sayings and New Thoughts," *Seminars in Cancer Biology* 21:139-146 (2011); Raposo et al., "Extracellular Vesicles: Exosomes, Microvesicles, and Friends," *The Journal of Cell Biology* 200:373-383 (2013); Skog et al., "Glioblastoma Microvesicles Transport RNA and Proteins That Promote Tumour Growth and Provide Diagnostic Biomarkers," *Nature Cell Biology* 10:1470-1476 (2008); van Niel et al., "Exosomes: A Common Pathway for a Specialized Function," *Journal of Biochemistry* 140:13-21 (2006)). Depending on the cell types they originate from, exosomes bear a specific protein and lipid composition (Choi et al., "Proteomics, Transcriptomics and Lipidomics of Exosomes and Ectosomes," *Proteomics* 13:1554-1571 (2013); Raposo et al., "Extracellular Vesicles: Exosomes, Microvesicles, and Friends," *The Journal of Cell Biology* 200:373-383 (2013); Stoorvogel et al., "The Biogenesis and Functions of Exosomes," *Traffic* 3:321-330 (2002)) and carry a select set of functional mRNAs, including micro RNAs (Valadi et al., "Exosome-mediated Transfer of mRNAs and microRNAs is a Novel Mechanism of Genetic Exchange Between Cells," *Nature Cell Biology* 9:654-659 (2007)). Moreover, retrotransposon RNA transcripts such as LINE-1 and Alu elements were transferred to normal cells via exosomes (Balaj et al., "Tumour Microvesicles Contain Retrotransposon Elements and Amplified Oncogene Sequences," *Nature Communications* 2:180 (2011)). Importantly, single-stranded DNA (ssDNA) harboring mutations reflecting the genetic status of the tumor cell as well as oncogene amplification (i.e. c-myc) has been detected in microvesicles (Balaj et al., "Tumour Microvesicles Contain Retrotransposon Elements and Amplified Oncogene Sequences," *Nature Communications* 2:180 (2011)). Cardiomyocyte microvesicles have been recently shown to secrete DNA and RNA promoting genetic changes in their microenvironment (Waldenstrom et al., "Cardiomyocyte Microvesicles Contain DNA/RNA and Convey Biological Messages to Target Cells," *PloS One* 7:e34653 (2012)). Interestingly, mitochondrial DNA has been also found in Astrocytes and Glioblastoma-derived microvesicles (Guescini et al., "Astrocytes and Glioblastoma Cells Release Exosomes Carrying mtDNA," *Journal of Neural Transmission* 117:1-4 (2010)).

During the process of pre-metastatic niche formation, bone marrow-derived cells (BMDCs) have been shown to constitute a crucial element in establishing a suitable microenvironment for the primary tumor and generation of metastasis (Kaplan et al., "VEGFR1-positive Haematopoietic Bone Marrow Progenitors Initiate the Pre-metastatic Niche," *Nature* 438:820-827 (2005); Kaplan et al., "Bone Marrow Cells in the 'Pre-metastatic Niche': Within Bone and Beyond," *Cancer Metastasis Reviews* 25:521-529 (2006); Psaila et al., "The Metastatic Niche: Adapting the Foreign Soil," *Nature Reviews Cancer* 9:285-293 (2009); Sethi et al., "Unravelling the Complexity of Metastasis—Molecular Understanding and Targeted Therapies," *Nature Reviews Cancer* 11:735-748 (2011)). Tumor-derived exosomes were recently identified as new factors reinforcing metastatic niche formation by permanently educating BMDCs toward increased metastatic and vasculogenic phenotypes (Peinado et al., "Melanoma Exosomes Educate Bone Marrow Progenitor Cells Toward a Pro-metastatic Phenotype Through MET," *Nature Medicine* 18:883-891 (2012)). The underlying cause of BMDC reprogramming was MET oncoprotein upregulation in BMDCs due to the influence and transference of MET positive secreted exosomes derived from highly metastatic melanoma models (Peinado et al., "Melanoma Exosomes Educate Bone Marrow Progenitor Cells Toward a Pro-metastatic Phenotype Through MET," *Nature Medicine* 18:883-891 (2012)). Furthermore, a melanoma specific exosome proteomic signature comprising TYRP2, VLA-4, HSP70 as well as the MET oncoprotein has been identified (Peinado et al., "Melanoma Exosomes Educate Bone Marrow Progenitor Cells Toward a Pro-metastatic Phenotype Through MET," *Nature Medicine* 18:883-891 (2012)). Because oncoproteins could be transferred to recipient cells, it was sought to determine whether tumor-derived DNA packaged in the exosome could also be transferred to normal stromal cells.

The present invention is directed to overcoming these and other deficiencies in the art.

SUMMARY OF THE INVENTION

A first aspect of the present invention is directed to a method for prognosing cancer in a subject. This method involves selecting a subject having cancer, obtaining a sample containing exosomes from the selected subject, recovering the exosomes from the sample, isolating double-stranded DNA from within the exosomes, and contacting the isolated double-stranded DNA with one or more reagents suitable to (1) detect presence or absence of one or more genetic mutations in the isolated double-stranded DNA that are associated with cancer, (2) quantify the amount of isolated double-stranded DNA from the recovered exosomes in the sample, (3) detect the methylation status of the isolated double-stranded DNA, or (4) quantify the amount of isolated double-stranded DNA able to enter a recipient cell. The cancer is prognosed based on the contacting.

Another aspect of the present invention is directed to a method of treating a subject having cancer. This method involves selecting a subject having cancer, obtaining a sample containing exosomes from the selected subject, recovering the exosomes from the sample, isolating double-stranded DNA from within the exosomes, and detecting (1)

the presence or absence of one or more genetic mutations in the isolated double-stranded DNA that are associated with cancer, (2) the amount of isolated double-stranded DNA from the recovered exosomes in the sample, (3) the methylation status of the isolated double-stranded DNA, or (4) the amount of isolated double-stranded DNA able to enter a recipient cell. A suitable cancer therapeutic is selected based on the detecting and is administered to the subject under conditions effective to treat the cancer.

Another aspect of the present invention is directed to a method of managing treatment of a subject having cancer. This method involves selecting a subject undergoing treatment for cancer, obtaining a sample containing exosomes from the selected subject, recovering the exosomes from the sample, isolating double-stranded DNA from within the exosomes, and detecting (1) the presence or absence of one or more genetic mutations in the isolated double-stranded DNA that are associated with cancer, (2) the amount of isolated double-stranded DNA from the recovered exosomes in the sample, (3) the methylation status of the isolated double-stranded DNA, or (4) the amount of isolated double-stranded DNA able to enter a recipient cell. Treatment is modified, as necessary, based on the detecting.

The present invention is based on the inventors' discovery that circulating tumor exosomes contain double-stranded DNA that phenocopies the mutational status of primary tumors and metastatic tumors. Accordingly, tumor derived exosomal double-stranded DNA can serve as a non-invasive, diagnostic and prognostic tool by facilitating the rapid genotyping of cancers to enable early detection and optimized treatment of disease. Importantly, diagnoses and prognoses are rendered feasible using this technique in cases where a biopsy is difficult to obtain (due to inaccessibility) or when a patient has multiple sites of disease. Moreover, this tool allows for frequent monitoring of the dynamics of tumor progression and molecular changes during treatment. In addition to prognostic and diagnostic utility, the molecular information gathered from exosomal double-stranded DNA analysis can be used to guide and develop personalized therapeutic regimes. Finally, because exosomes are secreted from tumors constitutively, and isolation of exosomes requires no special equipment, exosome double-stranded DNA-based testing can be readily employed in all standard laboratories.

In addition, the assessment of circulating cell-free (cf) DNA, bearing melanoma-specific mutations, has been proposed as a potentially useful prognostic marker (Sanmamed et al., "Quantitative Cell-free Circulating BRAFV600E Mutation Analysis by Use of Droplet Digital PCR in the Follow-up of Patients With Melanoma Being Treated With BRAF Inhibitors," *Clin. Chem.* 61(1):297-304 (2015); Schwarzenbach et al., "Clinical Relevance of Circulating Cell-free MicroRNAs in Cancer," *Nat. Rev. Clin. Oncol.* 11(3):145-156 (2014); Schwarzenbach et al., "Cell-free Nucleic Acids as Biomarkers in Cancer Patients," *Nat. Rev. Cancer* 11(6):426-437 (2011), which are hereby incorporated by reference in their entirety). Exosomal dsDNA represents the entire genomic DNA and represents an oncogenic profile corresponding to the mutational status of the primary tumor (Thakur et al., "Double-stranded DNA in Exosomes: a Novel Biomarker in Cancer Detection," *Cell Res.* 24(6):766-769 (2014), which is hereby incorporated by reference in its entirety) and is likely more stable compared to cfDNA due to its protection from nucleases in the serum by the exosomal membrane. Therefore, the present invention has potential to provide an improved measure of the mutational status of a primary tumor in metastatic capacity to predict cancer progression and recurrence. By investigating two novel parameters 1) level of exoDNA and 2) genetic alteration within exoDNA, the present invention advances existing prognostic tools in cancer and consequently improves stratification of cancer patients in terms of disease stage and risk of recurrence.

BRIEF DESCRIPTION OF THE DRAWINGS

As shown in FIG. 1D, internal exoDNA was extracted from exosomes secreted by different types of cancer cell lines including pancreatic cancer (Pan02, Pan02 H3, AsPC-1, PanCaco, BXPC-3 and HPAF-II), lung cancer (LLC, H1975 and H1650), breast cancer (MDA-MB-4175, MDA-MB-231 and 4T1 and E0771), melanoma (B16-F10) and leukemia (HL-60) (FIG. 1D). Abundance of dsDNA inside the exosomes, before and after digestion with dsDNase, was expressed as "nanogram of DNA per microgram of exoProtein".

In FIG. 2A, control digestion of ssDNA oligonucleotide and Lamda dsDNA was performed to verify the specificity of the enzymes. In FIG. 2B, total genomic DNA (gDNA) and exosomal DNA (exoDNA) isolated from K-562, HCT116 and B16F10 were quantified using QuantiFluor® dsDNA System, after the DNA samples were treated with either S1 nuclease or dsDNase. Control ssDNA oligonucleotide and dsDNA (Lamda DNA) were treated in parallel with either S1 nuclease or dsDNase.

FIG. 5A shows a circular view of the readings of fragments along each chromosome in the whole genome sequencing analysis of exoDNA isolated from murine melanoma B16-

F10 cell-derived exosomes. FIG. 5B shows a comparative Genomic Hybridization array analysis of B16F10 exoDNA vs. genomic DNA.

FIG. 7A shows BrdU-labeled exoDNA can be detected by immunofluorescence using anti-BrdU antibodies in NIH3T3 fibroblasts and lineage-negative bone marrow cells (Lin-BM). Cells were treated with BrdU-labeled B16F10 exosomes for 24 hours in vitro. FIG. 7B shows the transfer of BrdU-labeled exoDNA to blood cells and whole bone marrow (WBM) is shown by BrdU flow analysis 24 hours post tail vein injection of BrdU-labeled B16F10 exosomes.

FIG. 9A shows detection of BRAF V600E mutation in exoDNA isolated from melanoma cells harboring this mutation. AS-PCR was employed to detect the BRAF V600E mutation in the extracted exoDNA, with gDNA isolated from Sk-Mel-28 and Sk-Mel-103 cells as positive and negative controls for V600E mutation (WT (V) and mutant (E) alleles). Primers that distinguish the WT (V) and mutant (E) alleles of BRAF V600E mutation were used to amplify the target in the samples. Asterisk indicates the size of expected PCR products. The following cell lines were examined in this study for BRAF(V600E) mutation: wild-type: SK-Mel103, SK-Mel146 and SK-Mel 147; BRAF (V600E): SK-Mel 28, SK-Mel 133, SK-Mel 192, and SK-Mel 267. FIG. 9B shows detection of BRAF (V600E) mutation in circulating exoDNA isolated from melanoma-bearing NOD/SCID mice subcutaneously implanted with the human melanoma cell line, Sk-Mel-28) using AS-PCR assay as described in FIG. 9A.

FIGS. 11A and 11C shows confocal imaging of mouse bone marrow cells (FIG. 11A) and RAW 264.7 cells (FIG. 11C) pre-treated with EdU-labeled B16-F10 exosomes. FIGS. 11B and 11D show confocal imaging of mouse bone marrow cells (FIG. 11B) and RAW 264.7 cells (FIG. 11D) pre-treated with unlabeled exosomes. The left panels show DAPI staining (in grey) of nuclei, the middle panel shows the visualization of exosomal EdU-labeled DNA (in white) within the nucleus of the recipient cells, and the right panel shows overlay of the DAPI staining (in grey) and EdU-labeled DNA staining (in white). In FIGS. 11A-11D, Z-stack images of detected fluorescence from individual cells were taken to verify intra-nuclear localization of fluorescence signals.

DETAILED DESCRIPTION OF THE INVENTION

Figures 1A, 1B, 1C, 1D:
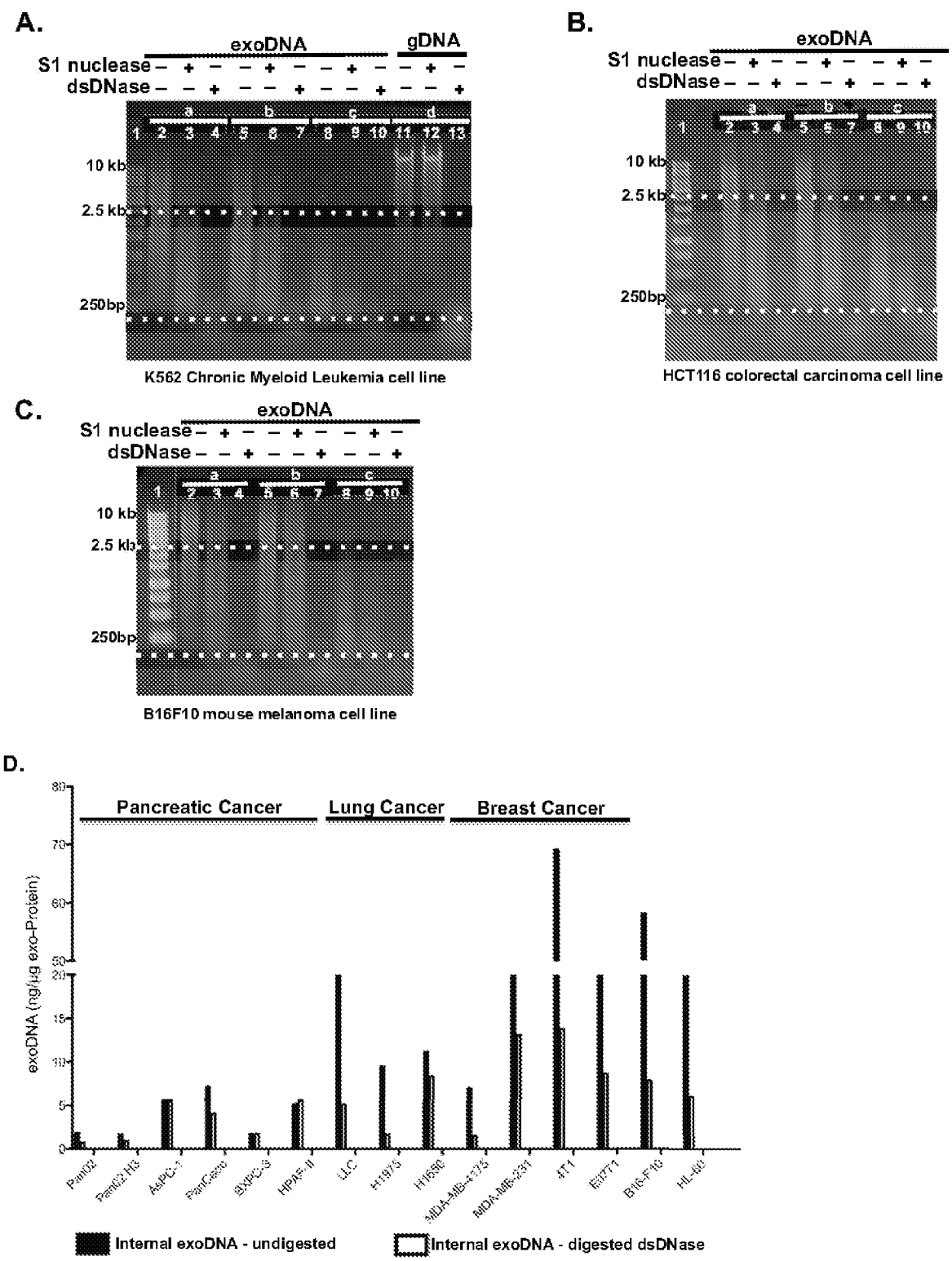
FIGS. 1A-1D show double-stranded DNA is associated with exosomes derived from different types of cancer cells. Exosomes were isolated from K-562 (FIG. 1A), HCT116 (FIG. 1B), and B16F10 (FIG. 1C) cell lines. Equal amounts of DNA extracted from untreated exosomes (Set a), exosomes treated with ssDNA specific S1 Nuclease (Set b) and exosomes treated with dsDNA specific Shrimp DNase (Set c) were digested with either S1 nuclease (lanes 3, 6 and 9) or dsDNase (lane 4, 7 and 10). Total genomic DNA from K-562 (FIG. 1A, Set d) was digested with S1 nuclease (Lane 12) or dsDNase (Lane 13). The results are representative of 2-3 experiments performed independently.

A first aspect of the present invention is directed to a method for prognosing cancer in a subject. This method involves selecting a subject having cancer, obtaining a sample containing exosomes from the selected subject, recovering the exosomes from the sample, isolating double-stranded DNA from within the exosomes, and contacting the isolated double-stranded DNA with one or more reagents suitable to (1) detect presence or absence of one or more genetic mutations in the isolated double-stranded DNA that are associated with cancer, (2) quantify the amount of isolated double-stranded DNA from the recovered exosomes in the sample, (3) detect the methylation status of the isolated double-stranded DNA, or (4) quantify the amount of isolated double-stranded DNA able to enter a recipient cell. The cancer is prognosed based on the contacting.

Cancer prognosis as described herein includes determining the probable progression and course of the cancerous condition, and determining the chances of recovery and survival of a subject with the cancer, e.g., a favorable prognosis indicates an increased probability of recovery and/or survival for the cancer patient, while an unfavorable prognosis indicates a decreased probability of recovery and/or survival for the cancer patient. A subject's prognosis can be determined or modified by the availability of a suitable treatment (i.e., a treatment that will increase the probability of recovery and survival of the subject with cancer). For example, if the subject has a cancer, such as melanoma that is positive for one or more BRAF mutations as described herein, the subject has a favorable prognosis, because he/she is a candidate for treatment with BRAF inhibitor therapy. Likewise, if the subject has lung cancer or other cancer that is positive for one or more EGFR mutations as described herein, the subject has a favorable prognosis, because he/she is a candidate for treatment with an EGFR inhibitor therapy. Accordingly, another aspect of the present invention includes selecting a suitable cancer therapeutic based on the determined prognosis and administering the selected therapeutic to the subject.

Prognosis also encompasses the metastatic potential of a cancer. For example, a favorable prognosis based on the presence or absence of a genetic phenotype can indicate that the cancer is a type of cancer having low metastatic potential, and the patient has an increased probability of long term recovery and/or survival. Alternatively, an unfavorable prognosis, based on the presence or absence of a genetic phenotype can indicate that the cancer is a type of cancer having a high metastatic potential, and the patient has a decreased probability of long term recovery and/or survival.

In accordance with this aspect of the present invention, and as described herein, exosomes derived from tumors having high metastatic potential contain much higher levels of double-stranded DNA (dsDNA) within the exosome than exosomes derived from tumors having a low or no metastatic potential. Therefore, in one embodiment of the present invention, a reference or standard exosomal sample is an exosomal sample derived from tumor cells known to have low metastatic potential such as B16F1 melanoma cells, H1975 and H1650 lung cancer cells, or U87 glioblastoma cells. A higher concentration of DNA in the exosomal sample from the subject as compared to the concentration of dsDNA in exosomes derived from cells of low metastatic potential indicates the subject has a cancer with a high metastatic potential. If the exosomal sample from the subject has the same or lower concentration of dsDNA as compared to the concentration of dsDNA in exosomes derived from cells of low metastatic potential, then the subject has a cancer with a low metastatic potential. Alternatively, a reference or standard exosomal sample can be derived from tumor cells having a high metastatic potential, such as B16F10 melanoma cells or Lewis lung carcinoma cells. If the exosomal sample from the subject has the same or higher concentration of dsDNA as compared to exosomes derived from tumor cells of high metastatic potential, then the subject has a cancer with high metastatic potential. If the exosomal sample from the subject has a lower concentration of dsDNA as compared to exosomes derived from tumor cells of high metastatic potential, then the subject has a cancer with low metastatic potential.

Prognosis further encompasses prediction of sites of metastasis, determination of the stage of the cancer, or identifying the location of a primary tumor in a subject.

A change in the mutational status of gene associated with cancer (e.g., BRAF and/or EGFR) indicates that a change in the cancer phenotype has occurred with disease progression. For example, detecting the presence of a BRAF and/or EGFR mutation in an exosomal dsDNA sample from a subject whereas no BRAF and/or EGFR mutation was detected in an earlier exosomal dsDNA sample obtained from the same subject, can be indicative of a particular site of metastasis or progression to a more advanced stage of the cancer. Therefore, periodic monitoring of exosomal dsDNA mutational status provides a means for detecting primary tumor progression, metastasis, and facilitating optimal targeted or personalized treatment of the cancerous condition.

The detection of certain exosomal dsDNA mutations in a metastatic cancer sample can also identify the location of a primary tumor. For example, the detection of one or more BRAF mutations in a metastatic tumor or cancer cell-derived exosomal sample indicates that the primary tumor or cancer was melanoma or a form of brain cancer, e.g. glioblastoma. The detection of one or more EGFR mutations in a metastatic tumor or cancer cell derived exosomal dsDNA sample indicates that the primary tumor originated in the lung, or alternatively the primary cancer was head and neck cancer, ovarian cancer, cervical cancer, bladder cancer, or esophageal cancer.

Another aspect of the present invention is directed to a method of treating a subject having cancer. This method involves selecting a subject having cancer, obtaining a sample containing exosomes from the selected subject, recovering the exosomes from the sample, isolating double-stranded DNA from within the exosomes, and detecting (1) the presence or absence of one or more genetic mutations in the isolated double-stranded DNA that are associated with cancer, (2) the amount of isolated double-stranded DNA from the recovered exosomes in the sample, (3) the methylation status of the isolated double-stranded DNA, or (4) the amount of isolated double-stranded DNA able to enter a recipient cell. A suitable cancer therapeutic is selected based on the detecting and is administered to the selected subject under conditions effective to treat the cancer.

Another aspect of the present invention is directed to a method of managing treatment of a subject having cancer. This method involves selecting a subject undergoing treatment for cancer, obtaining a sample containing exosomes from the selected subject, recovering the exosomes from the sample, isolating double-stranded DNA from within the exosomes, and detecting (1) the presence or absence of one or more genetic mutations in the isolated double-stranded DNA that are associated with cancer, (2) the amount of isolated double-stranded DNA from the recovered exosomes in the sample, (3) the methylation status of the isolated double-stranded DNA, or (4) the amount of isolated double-stranded DNA able to enter a recipient cell. Treatment is modified, as necessary, based on the detecting.

In accordance with all aspects of the present invention, a "subject" or "patient" encompasses any animal, but preferably a mammal, e.g., human, non-human primate, a dog, a cat, a horse, a cow, or a rodent. More preferably, the subject or patient is a human. In some embodiments of the present invention, the subject has cancer, for example and without limitation, melanoma, breast cancer, lung cancer, or leukemia. In some embodiments, the cancer is a primary tumor, while in other embodiments, the cancer is a secondary or metastatic tumor.

"Exosomes" are microvesicles released from a variety of different cells, including cancer cells (i.e., "cancer-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process.

In accordance with the methods of the present invention, exosomes can be isolated or obtained from most biological fluids including, without limitation, blood, serum, plasma, ascites, cyst fluid, pleural fluid, peritoneal fluid, cerebral spinal fluid, tears, urine, saliva, sputum, nipple aspirates, lymph fluid, fluid of the respiratory, intestinal, and genitourinary trances, breast milk, intra-organ system fluid, or combinations thereof.

An enriched population of exosomes can be obtained from a biological sample using methods known in the art. For example, exosomes may be concentrated or isolated from a biological sample using size exclusion chromatography, density gradient centrifugation, differential centrifugation (Raposo et al. "B lymphocytes Secrete Antigen-presenting Vesicles," *J Exp Med* 183(3): 1161-72 (1996), which is hereby incorporated by reference in its entirety), anion exchange and/or gel permeation chromatography (for example, as described in U.S. Pat. No. 6,899,863 to Dhellin et al., and U.S. Pat. No. 6,812,023 to Lamparski et al., which are hereby incorporated by reference in their entirety), sucrose density gradients or organelle electrophoresis (for example, as described in U.S. Pat. No. 7,198,923), magnetic activated cell sorting (MACS) (Taylor et al., "MicroRNA Signatures of Tumor-derived Exosomes as Diagnostic Biomarkers of Ovarian Cancer," *Gynecol Oncol* 110(1): 13-21 (2008), which is hereby incorporated by reference in its entirety), nanomembrane ultrafiltration (Cheruvanky et al., "Rapid Isolation of Urinary Exosomal Biomarkers using a Nanomembrane Ultrafiltration Concentrator," *Am J Physiol Renal Physiol* 292(5): F1657-61 (2007), which is hereby incorporated by reference in its entirety), immunoabsorbent capture, affinity purification, microfluidic separation, or combinations thereof.

Exosomes isolated from a bodily fluid (i.e., peripheral blood, cerebrospinal fluid, urine) can be enriched for those originating from a specific cell type, for example, lung, pancreas, stomach, intestine, bladder, kidney, ovary, testis, skin, colorectal, breast, prostate, brain, esophagus, liver, placenta, and fetal cells. Because the exosomes often carry surface molecules such as antigens from their donor cells, surface molecules may be used to identify, isolate and/or enrich for exosomes from a specific donor cell type. In this way, exosomes originating from distinct cell populations can be analyzed for their nucleic acid content. For example, tumor (malignant and non-malignant) exosomes carry tumor-associated surface antigens and these exosomes can be isolated and/or enriched via these specific tumor-associated surface antigens. In one example, the tumor-associated surface antigen is epithelial-celladhesion-molecule (Ep-CAM), which is specific to exosomes from carcinomas of lung, colorectal, breast, prostate, head and neck, and hepatic origin, but not of hematological cell origin (Balzar et al. "The Biology of the 17-1A Antigen (Ep-CAM)," *J Mol Med* 77(10): 699-712 (1999); Went et al. "Frequent EpCam Protein Expression in Human Carcinomas," *Hum Pathol* 35(1): 122-8 (2004), which are hereby incorporated by reference in their entirety). In another example, the surface antigen is CD24, which is a glycoprotein specific to urine microvesicles (Keller et al. "CD24 is a Marker of Exosomes Secreted into Urine and Amniotic Fluid," *Kidney Int* 72(9): 1095-102 (2007), which is hereby incorporated by reference in its entirety). In yet another example, the surface antigen is CD70, carcinoembryonic antigen (CEA), EGFR, EGFRvIII and other variants, Fas ligand, TRAIL, tranferrin receptor, p38.5, p97 and HSP72. Alternatively, tumor specific exosomes may be characterized by the lack of surface markers, such as the lack of CD80 and CD86 expression.

The isolation of exosomes from specific cell types can be accomplished, for example, by using antibodies, aptamers, aptamer analogs, or molecularly imprinted polymers specific for a desired surface antigen. In one embodiment, the surface antigen is specific for a cancer type. In another embodiment, the surface antigen is specific for a cell type which is not necessarily cancerous. One example of a method of exosome separation based on cell surface antigen is provided in U.S. Pat. No. 7,198,923, which is hereby incorporated by reference in its entirety. As described in, e.g., U.S. Pat. No. 5,840,867 to Toole and U.S. Pat. No. 5,582,981 to Toole, which are hereby incorporated by reference in their entirety, aptamers and their analogs specifically bind surface molecules and can be used as a separation tool for retrieving cell type-specific exosomes. Molecularly imprinted polymers also specifically recognize surface molecules as described in, e.g., U.S. Pat. Nos. 6,525,154, 7,332,553 and 7,384,589, which are hereby incorporated by reference in their entirety, and are a tool for retrieving and isolating cell type-specific exosomes.

The exosomal fraction from a bodily fluid of a subject can be pre-treated with DNase to eliminate or substantially eliminate any DNA located on the surface or outside of the exosomes. Without DNAse pre-treatment, short DNA fragments on the outside of the exosomes may remain and co-isolate with nucleic acids extracted from inside the exosomes. Thus, elimination of all or substantially all DNA associated with the outside or surface of the exosomes by pre-treatment of with DNase, has the ability to enrich for internal exosomal dsDNA. To distinguish DNA stranded-ness within exosomes, Shrimp DNase specifically digests double-stranded DNA and S1 nuclease specifically digests single-stranded DNA.

In accordance with this and all other aspects of the present invention, the double-stranded DNA may be isolated by extracting the DNA from the exosomes prior to or for analysis.

The extracted dsDNA can be analyzed directly without an amplification step. Direct analysis may be performed with different methods including, but not limited to, nanostring technology. NanoString technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. The technology is described in a publication by Geiss et al. "Direct Multiplexed Measurement of Gene Expression with Color-Coded Probe Pairs," *Nat* Biotechnol 26(3): 317-25 (2008), which is hereby incorporated by reference in its entirety.

In another embodiment, it may be beneficial or otherwise desirable to amplify the nucleic acid of the exosome prior to analyzing it. Methods of nucleic acid amplification are commonly used and generally known in the art. If desired, the amplification can be performed such that it is quantitative. Quantitative amplification will allow quantitative determination of relative amounts of the various exosomal nucleic acids.

Nucleic acid amplification methods include, without limitation, polymerase chain reaction (PCR) (U.S. Pat. No. 5,219,727, which is hereby incorporated by reference in its entirety) and its variants such as in situ polymerase chain reaction (U.S. Pat. No. 5,538,871, which is hereby incorporated by reference in its entirety), quantitative polymerase chain reaction (U.S. Pat. No. 5,219,727, which is hereby incorporated by reference in its entirety), nested polymerase chain reaction (U.S. Pat. No. 5,556,773, which is hereby incorporated by reference in its entirety), self sustained sequence replication and its variants (Guatelli et al. "Isothermal, In vitro Amplification of Nucleic Acids by a Multienzyme Reaction Modeled after Retroviral Replication," *Proc Natl Acad Sci USA* 87(5): 1874-8 (1990), which is hereby incorporated by reference in its entirety), transcriptional amplification system and its variants (Kwoh et al. "Transcription-based Amplification System and Detection of Amplified Human Immunodeficiency Virus type 1 with a Bead-Based Sandwich Hybridization Format," *Proc Natl Acad Sci USA* 86(4): 1173-7 (1989), which is hereby incorporated by reference in its entirety), Qb Replicase and its variants (Miele et al. "Autocatalytic Replication of a Recombinant RNA." *J Mol Biol* 171(3): 281-95 (1983), which is hereby incorporated by reference in its entirety), cold-PCR (Li et al. "Replacing PCR with COLD-PCR Enriches Variant DNA Sequences and Redefines the Sensitivity of Genetic Testing." *Nat Med* 14(5): 579-84 (2008), which is hereby incorporated by reference in its entirety) or any other nucleic acid amplification and detection methods known to those of skill in the art. Especially useful are those detection schemes designed for the detection of nucleic acid molecules if such molecules are present in very low numbers.

In one embodiment, the isolated double-stranded DNA is contacted with one or more reagents suitable to detect the presence or absence of one or more genetic mutations in the isolated double-stranded DNA that are associated with cancer. Exemplary genetic mutations associated with cancer include, but are not limited to, BRAF, EGFR, APC, NOTCH1, HRAS, KRAS, NRAS, MET, p.53, PTEN, HER2, FLT3, BRCA1, BRCA2, PIK3CA, KIT, RET, AKT, ABL, CDK4, MYC, RAF, PDGFR, BCR-ABL, NPM1, CEBPalpha, and SRC.

The one or more mutations in the one or more identified genes can be detected using a hybridization assay. In a hybridization assay, the presence or absence of a gene mutation is determined based on the hybridization of one or more allele-specific oligonucleotide probes to one or more nucleic acid molecules in the exosomal dsDNA sample from the subject. The oligonucleotide probe or probes comprise a nucleotide sequence that is complementary to at least the region of the gene that contains the mutation of interest. The oligonucleotide probes are designed to be complementary to the wildtype, non-mutant nucleotide sequence and/or the mutant nucleotide sequence of the one or more genes to effectuate the detection of the presence or the absence of the mutation in the sample from the subject upon contacting the sample with the oligonucleotide probes. A variety of hybridization assays that are known in the art are suitable for use in the methods of the present invention. These methods include, without limitation, direct hybridization assays, such as northern blot or Southern blot (see e.g., Ausabel et al., Current Protocols in Molecular Biology, John Wiley & Sons, NY (1991), which is hereby incorporated by reference in its entirety). Alternatively, direct hybridization can be carried out using an array based method where a series of oligonucleotide probes designed to be complementary to a particular non-mutant or mutant gene region are affixed to a solid support (glass, silicon, nylon membranes). A labeled exosomal DNA or cDNA sample from the subject is contacted with the array containing the oligonucleotide probes, and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array. Alternatively, the sample is bound to a solid support (often DNA or PCR amplified DNA) and labeled with oligonucleotides in solution (either allele specific or short so as to allow sequencing by hybridization).

Other common genotyping methods include, but are not limited to, restriction fragment length polymorphism assays; amplification based assays such as molecular beacon assays, nucleic acid arrays, high resolution melting curve analysis (Reed and Wittwer, "Sensitivity and Specificity of Single-Nucleotide Polymorphism Scanning by High Resolution Melting Analysis," *Clinical Chem* 50(10): 1748-54 (2004), which is hereby incorporated by reference in its entirety); allele-specific PCR (Gaudet et al., "Allele-Specific PCR in SNP Genotyping," *Methods Mol Biol* 578: 415-24 (2009), which is hereby incorporated by reference in its entirety); primer extension assays, such as allele-specific primer extension (e.g., Illumina® Infinium® assay), arrayed primer extension (see Krjutskov et al., "Development of a Single Tube 640-plex Genotyping Method for Detection of Nucleic Acid Variations on Microarrays," *Nucleic* Acids Res. 36(12) e75 (2008), which is hereby incorporated by reference in its entirety), homogeneous primer extension assays, primer extension with detection by mass spectrometry (e.g., Sequenom® iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety), multiplex primer extension sorted on genetic arrays; flap endonuclease assays (e.g., the Invader® assay) (see Olivier M., "The Invader Assay for SNP Genotyping," *Mutat. Res.* 573 (1-2) 103-10 (2005), which is hereby incorporated by reference in its entirety); 5' nuclease assays, such as the TaqMan® assay (see U.S. Pat. No. 5,210,015 to Gelfand et al. and U.S. Pat. No. 5,538,848 to Livak et al., which are hereby incorporated by reference in their entirety); and oligonucleotide ligation assays, such as ligation with rolling circle amplification, homogeneous ligation, OLA (see U.S. Pat. No. 4,988,617 to Landgren et al., which is hereby incorporated by reference in its entirety), multiplex ligation reactions followed by PCR, wherein zipcodes are incorporated into ligation reaction probes, and amplified PCR products are determined by electrophoretic or universal zipcode array readout (see U.S. Pat. Nos. 7,429,453 and 7,312,039 to Barany et al., which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection. In general, the methods for analyzing genetic aberrations are reported in numerous publications, not limited to those cited herein, and are available to those skilled in the art. The appropriate method of analysis will depend upon the specific goals of the analysis, the condition/history of the patient, and the specific cancer(s), diseases or other medical conditions to be detected, monitored or treated.

Alternatively, the presence or absence of one or more mutations identified supra can be detected by direct sequencing of the genes, or preferably particular gene regions comprising the one or more identified mutations, from the patient sample. Direct sequencing assays typically involve isolating DNA sample from the subject using any suitable method known in the art, and cloning the region of interest to be sequenced into a suitable vector for amplification by growth in a host cell (e.g. bacteria) or direct amplification by PCR or other amplification assay. Following amplification, the DNA can be sequenced using any suitable method. A preferable sequencing method involves high-throughput next generation sequencing (NGS) to identify genetic variation. Various NGS sequencing chemistries are available and suitable for use in carrying out the claimed invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™) Alternatively, classic sequencing methods, such as the Sanger chain termination method or Maxam-Gilbert sequencing, which are well known to those of skill in the art, can be used to carry out the methods of the present invention.

In one embodiment of the present invention, the selected subject has melanoma, and the presence or absence of a mutation in BRAF is detected in an exosomal dsDNA sample from the subject. BRAF is a serine/threonine protein kinase that is encoded on chromosome 7q34. The amino acid sequence and nucleotide sequence of human BRAF are provided below as SEQ ID NO: 1 and SEQ ID NO: 2, respectively.

Human BRAF
SEQ ID NO: 1

Met Ala Ala Leu Ser Gly Gly Gly Gly Ala Glu Pro Gly Gln
1               5                   10              15

Ala Leu Phe Asn Gly Asp Met Glu Pro Glu Ala Gly Ala Gly
            20              25              30

Ala Ala Ala Ser Ser Ala Ala Asp Pro Ala Ile Pro Glu Val Trp
        35              40              45

Asn Ile Lys Gln Met Ile Lys Leu Thr Gln Glu His Ile Glu Ala Leu
50              55              60

Leu Asp Lys Phe Gly Gly Glu His Asn Pro Pro Ser Ile Tyr Leu Glu
65              70              75              80

Ala Tyr Glu Glu Tyr Thr Ser Lys Leu Asp Ala Leu Gln Gln Arg Glu
                85              90              95

Gln Gln Leu Leu Glu Ser Leu Gly Asn Gly Thr Asp Phe Ser Val Ser
            100             105             110

Ser Ser Ala Ser Met Asp Thr Val Thr Ser Ser Ser Ser Ser Ser Leu
            115             120             125

Ser Val Leu Pro Ser Ser Leu Ser Val Phe Gln Asn Pro Thr Asp Val
    130             135             140

Ala Arg Ser Asn Pro Lys Ser Pro Gln Lys Pro Ile Val Arg Val Phe
145             150             155             160

Leu Pro Asn Lys Gln Arg Thr Val Val Pro Ala Arg Cys Gly Val Thr
                165             170             175

Val Arg Asp Ser Leu Lys Lys Ala Leu Met Met Arg Gly Leu Ile Pro
            180             185             190

Glu Cys Cys Ala Val Tyr Arg Ile Gln Asp Gly Glu Lys Lys Pro Ile
            195             200             205

Gly Trp Asp Thr Asp Ile Ser Trp Leu Thr Gly Glu Glu Leu His Val
        210             215             220

Glu Val Leu Glu Asn Val Pro Leu Thr Thr His Asn Phe Val Arg Lys
225             230             235             240

Thr Phe Phe Thr Leu Ala Phe Cys Asp Phe Cys Arg Lys Leu Leu Phe
                245             250             255

Gln Gly Phe Arg Cys Gln Thr Cys Gly Tyr Lys Phe His Gln Arg Cys
            260             265             270

Ser Thr Glu Val Pro Leu Met Cys Val Asn Tyr Asp Gln Leu Asp Leu
            275             280             285

Leu Phe Val Ser Lys Phe Phe Glu His His Pro Ile Pro Gln Glu Glu
        290             295             300

Ala Ser Leu Ala Glu Thr Ala Leu Thr Ser Gly Ser Ser Pro Ser Ala
305             310             315             320

Pro Ala Ser Asp Ser Ile Gly Pro Gln Ile Leu Thr Ser Pro Ser Pro
                325             330             335

Ser Lys Ser Ile Pro Ile Pro Gln Pro Phe Arg Pro Ala Asp Glu Asp
            340             345             350

His Arg Asn Gln Phe Gly Gln Arg Asp Arg Ser Ser Ala Pro Asn
            355             360             365

Val His Ile Asn Thr Ile Glu Pro Val Asn Ile Asp Asp Leu Ile Arg
    370             375             380

Asp Gln Gly Phe Arg Gly Asp Gly Gly Ser Thr Thr Gly Leu Ser Ala
385             390             395             400

Thr Pro Pro Ala Ser Leu Pro Gly Ser Leu Thr Asn Val Lys Ala Leu
                405             410             415

Gln Lys Ser Pro Gly Pro Gln Arg Glu Arg Lys Ser Ser Ser Ser Ser

-continued

```
                420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
        450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
            485                 490                 495
Ala Phe Lys Asn Glu Val Gly Val Leu Arg Lys Thr Arg His Val Asn
        500                 505                 510
Ile Leu Leu Phe Met Gly Tyr Ser Thr Lys Pro Gln Leu Ala Ile Val
        515                 520                 525
Thr Gln Trp Cys Glu Gly Ser Ser Leu Tyr His His Leu His Ile Ile
        530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
            565                 570                 575
Leu Lys Ser Asn Asn Ile Phe Leu His Glu Asp Leu Thr Val Lys Ile
        580                 585                 590
Gly Asp Phe Gly Leu Ala Thr Val Lys Ser Arg Trp Ser Gly Ser His
        595                 600                 605
Gln Phe Glu Gln Leu Ser Gly Ser Ile Leu Trp Met Ala Pro Glu Val
        610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
            645                 650                 655
Ser Asn Ile Asn Asn Arg Asp Gln Ile Ile Phe Met Val Gly Arg Gly
        660                 665                 670
Tyr Leu Ser Pro Asp Leu Ser Lys Val Arg Ser Asn Cys Pro Lys Ala
        675                 680                 685
Met Lys Arg Leu Met Ala Glu Cys Leu Lys Lys Lys Arg Asp Glu Arg
        690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
            725                 730                 735
Gly Phe Gln Thr Glu Asp Phe Ser Leu Tyr Ala Cys Ala Ser Pro Lys
        740                 745                 750
Thr Pro Ile Gln Ala Gly Gly Tyr Gly Ala Phe Pro Val His
        755                 760                 765
Human BRAF
                                                                SEQ ID NO: 2
cgcctcccctt ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccgaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgattttc tgtttctagc tctgcatcaa tggataccgt     420
```

```
                             -continued
tacatcttct tcctcttcta gcctttcagt gctaccttca tctctttcag ttttcaaaa    480 tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780 aacgttttc  accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
acccgcctcg gactctattg ggccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc ccaatgtgca tataaacaca atagaacctg tcaatattga   1200
tgacttgatt agagaccaag gatttcgtgg tgatggagga tcaaccacag gtttgtctgc   1260
taccccccct gcctcattac ctggctcact aactaacgtg aaagccttac agaaatctcc   1320
aggacctcag cgagaaagga agtcatcttc atcctcagaa gacaggaatc gaatgaaaac   1380
acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact tacacgccaa gtcaatcatc cacagagacc tcaagagtaa   1800
taatatattt cttcatgaag acctcacagt aaaaatagt  gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggata    2340 tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggatttta  acatccaagg gttaaaatac atagacattg   2580
ctaaaaattg gcagagcctc ttctagaggc tttactttct gttccgggtt tgtatcattc   2640
acttggttat tttaagtagt aaacttcagt ttctcatgca acttttgttg ccagctatca   2700
catgtccact agggactcca gaagaagacc ctacctatgc ctgtgtttgc aggtgagaag   2760
ttggcagtcg gttagcctgg gttagataag gcaaactgaa cagatctaat ttaggaagtc   2820
agtagaattt aataattcta ttattattct taataatttt tctataacta tttctttta   2880
```

```
taacaatttg gaaaatgtgg atgtctttta tttccttgaa gcaataaact aagtttcttt    2940
ttataaaaa                                                            2949
```

BRAF activates the MAP kinase/ERK-signaling pathway, and mutations in BRAF are associated with approximately 50% of pediatric and adult malignant melanomas (Daniotti et al., "Cutaneous Melanoma in Childhood and Adolescence Shows Frequent Loss of INK4A and Gain of KIT," *J. Invest. Dermatol.* 129 (7): 1759-68 (2009), which is hereby incorporated by reference in its entirety). In addition, BRAF point mutations have been reported to occur in several low- and high-grade tumor types in pediatric and adult patients, including approximately 50-60% of gangliogliomas (Mac-Conaill et al., "Profiling Critical Cancer Gene Mutations in Clinical Tumor Samples," *PloSOne* 4(11):e7887 (2009), and Dougherty et al. "Activating Mutations in BRAF Characterize a Spectrum of Pediatric Low-Grade Gliomas," *Neuro Oncol* 12 (7): 621-630 (2010), which are hereby incorporated by reference in their entirety), approximately 2-12% of pilocytic astrocytomas (Forshew et al., "Activation of the ERK/MAPK Pathway: A Signature Genetic Defect in Posterior Fossa Pilocytic Astrocytomas," *J Pathol.* 218:172-181 (2009); Pfister et al., "BRAF Gene Duplication Constitutes a Mechanism of MAPK Pathway Activation in Low-Grade Astrocytomas," *J Clin Invest.* 118:1739-1749 (2008); Mac-Conaill et al., "Profiling Critical Cancer Gene Mutations in Clinical Tumor Samples," *PloSOne* 4(11):e7887 (2009); Qaddoumi et al., "Paediatric Low-Grade Gliomas and the Need for New Options for Therapy," *Cancer Biol Ther.* 8:1-7 (2009); Jacob et al., "Duplication of 7q34 is Specific to Juvenile Pilocytic Astrocytomas and a Hallmark of Cerebellar and Optic Pathway Tumors," *Brit J Cancer;* 101:722-733 (2009); and Dias-Santagata et al., "BRAF V600E Mutations Are Common in Pleomorphic Xanthoastrocytoma: Diagnostic and Therapeutic Implications," *PLoS ONE* 6(3): e17948 (2011), which are hereby incorporated by reference in their entirety), and in as many as 30% of high-grade astrocytomas. Glioma accounts for 90% of malignant central nervous system (CNS) tumors in adults and 50% in the pediatric population (Central Brain Tumor Registry of the United States, 2010).

Over 90% of BRAF mutations in melanoma are at amino acid residue 600 (SEQ ID NO: 1), and over 90% of these involve a single nucleotide mutation that causes a valine glutamic acid change (BRAF V600E: nucleotide 1799 T>A of SEQ ID NO: 2; codon GTG>GAG) (Ascierto et al., "The Role of BRAF V600 Mutation in Melanoma," *J. Translational Med.* 10:85 (2012), which is hereby incorporated by reference in its entirety). Other mutations at this same valine residue of BRAF include a lysine substitution (BRAFV600K), an arginine substitution (BRAFV600R), and an aspartic acid substitution (BRAFV600D). The detection of any one of these BRAF V600 mutations, or other known BRAF mutations (i.e., insertions, deletions, duplications, etc.) in an exosomal DNA sample from a subject has diagnostic/prognostic and therapeutic implications in accordance with the methods of the present invention.

The BRAF V600 mutations cause constitutive activation of BRAF, which leads to activation of the downstream MEK/ERK pathway, evasion of senescence and apoptosis, uncheck replicative potential, angiogenesis, tissue invasion, metastasis, as well as evasion of immune response (Maurer et al., "Raf Kinases in Cancer-Roles and Therapeutic Opportunities," *Oncogene* 30: 3477-3488 (2011), which is hereby incorporated by reference in its entirety). Melanoma patients and patients having brain cancer identified as having a BRAF V600 mutation or other BRAF activating mutations are candidates for treatment with a BRAF inhibitor, such as vemurafenib (PLX/RG7204/RO5185426) (Sosman et al., "Survival in BRAF V600-Mutant Advanced Melanoma Treated with Vemurafenib," *N Engl J Med* 366:707-14 (2012) and Chapman et al., "Improved Survival with Vemurafenib in Melanoma with BRAF V600E Mutation," *N Engl J Med* 364"2507-2516 (2011), which are hereby incorporated by reference in their entirety), dabrafenib (Tafinlar; GSK2118436) (Gibney et al., "Clinical Development of Dabrafenib in BRAF mutant Melanoma and Other Malignancies" *Expert Opin Drug Metab Toxicol* 9(7):893-9 (2013), which is hereby incorporated by reference in its entirety), RAF265 (Su et al., "RAF265 Inhibits the Growth of Advanced Human Melanoma Tumors," *Clin Cancer Res* 18(8): 2184-98 (2012), which is hereby incorporated by reference in its entirety), and LGX818 (Stuart et al., "Preclinical Profile of LGX818: A Potent and Selective RAF Kinase Inhibitor," *Cancer Res* 72(8) Suppl 1 (2012), which is hereby incorporated by reference in its entirety).

In another embodiment of the present invention, the presence or absence of one or more mutations in the epidermal growth factor receptor (EGFR) is detected. EGFR is a transmembrane glycoprotein with an extracellular ligand-binding domain and an intracellular domain possessing intrinsic tyrosine kinase activity. Upon receptor dimerization following ligand binding, the tyrosine kinase domain is activated and recruited for phosphorylation of intracellular targets that drive normal cell growth and differentiation. The amino acid sequence and nucleotide sequence of human EGFR are provided below as SEQ ID NO: 3 and SEQ ID NO: 4, respectively.

```
Human EGFR
                                                              SEQ ID NO: 3
Arg Pro Ser Gly Thr Ala Gly Ala Ala Leu Leu Ala Leu Leu Ala Ala
1               5                   10                  15

Leu Cys Pro Ala Ser Arg Ala Leu Glu Glu Lys Lys Val Cys Gln Gly
            20                  25                  30

Thr Ser Asn Lys Leu Thr Gln Leu Gly Thr Phe Glu Asp His Phe Leu
        35                  40                  45

Ser Leu Gln Arg Met Phe Asn Asn Cys Glu Val Val Leu Gly Asn Leu
    50                  55                  60
```

-continued

```
Glu Ile Thr Tyr Val Gln Arg Asn Tyr Asp Leu Ser Phe Leu Lys Thr
 65                  70                  75                  80

Ile Gln Glu Val Ala Gly Tyr Val Leu Ile Ala Leu Asn Thr Val Glu
                 85                  90                  95

Arg Ile Pro Leu Glu Asn Leu Gln Ile Ile Arg Gly Asn Met Tyr Tyr
            100                 105                 110

Glu Asn Ser Tyr Ala Leu Ala Val Leu Ser Asn Tyr Asp Ala Asn Lys
        115                 120                 125

Thr Gly Leu Lys Glu Leu Pro Met Arg Asn Leu Gln Glu Ile Leu His
130                 135                 140

Gly Ala Val Arg Phe Ser Asn Asn Pro Ala Leu Cys Asn Val Glu Ser
145                 150                 155                 160

Ile Gln Trp Arg Asp Ile Val Ser Ser Asp Phe Leu Ser Asn Met Ser
                165                 170                 175

Met Asp Phe Gln Asn His Leu Gly Ser Cys Gln Lys Cys Asp Pro Ser
            180                 185                 190

Cys Pro Asn Gly Ser Cys Trp Gly Ala Gly Glu Glu Asn Cys Gln Lys
        195                 200                 205

Leu Thr Lys Ile Ile Cys Ala Gln Gln Cys Ser Gly Arg Cys Arg Gly
    210                 215                 220

Lys Ser Pro Ser Asp Cys Cys His Asn Gln Cys Ala Ala Gly Cys Thr
225                 230                 235                 240

Gly Pro Arg Glu Ser Asp Cys Leu Val Cys Arg Lys Phe Arg Asp Glu
                245                 250                 255

Ala Thr Cys Lys Asp Thr Cys Pro Pro Leu Met Leu Tyr Asn Pro Thr
            260                 265                 270

Thr Tyr Gln Met Asp Val Asn Pro Glu Gly Lys Tyr Ser Phe Gly Ala
        275                 280                 285

Thr Cys Val Lys Lys Cys Pro Arg Asn Tyr Val Val Thr Asp His Gly
    290                 295                 300

Ser Cys Val Arg Ala Cys Gly Ala Asp Ser Tyr Glu Met Glu Glu Asp
305                 310                 315                 320

Gly Val Arg Lys Cys Lys Lys Cys Glu Gly Pro Cys Arg Lys Val Cys
                325                 330                 335

Asn Gly Ile Gly Ile Gly Glu Phe Lys Asp Ser Leu Ser Ile Asn Ala
            340                 345                 350

Thr Asn Ile Lys His Phe Lys Asn Cys Thr Ser Ile Ser Gly Asp Leu
        355                 360                 365

His Ile Leu Pro Val Ala Phe Arg Gly Asp Ser Phe Thr His Thr Pro
    370                 375                 380

Pro Leu Asp Pro Gln Glu Leu Asp Ile Leu Lys Thr Val Lys Glu Ile
385                 390                 395                 400

Thr Gly Phe Leu Leu Ile Gln Ala Trp Pro Glu Asn Arg Thr Asp Leu
                405                 410                 415

His Ala Phe Glu Asn Leu Glu Ile Ile Arg Gly Arg Thr Lys Gln His
            420                 425                 430

Gly Gln Phe Ser Leu Ala Val Val Ser Leu Asn Ile Thr Ser Leu Gly
        435                 440                 445

Leu Arg Ser Leu Lys Glu Ile Ser Asp Gly Asp Val Ile Ile Ser Gly
    450                 455                 460

Asn Lys Asn Leu Cys Tyr Ala Asn Thr Ile Asn Trp Lys Lys Leu Phe
465                 470                 475                 480

Gly Thr Ser Gly Gln Lys Thr Lys Ile Ile Ser Asn Arg Gly Glu Asn
                485                 490                 495
```

-continued

```
Ser Cys Lys Ala Thr Gly Gln Val Cys His Ala Leu Cys Ser Pro Glu
            500                 505                 510
Gly Cys Trp Gly Pro Glu Pro Arg Asp Cys Val Ser Cys Arg Asn Val
        515                 520                 525
Ser Arg Gly Arg Glu Cys Val Asp Lys Cys Asn Leu Leu Glu Gly Glu
    530                 535                 540
Pro Arg Glu Phe Val Glu Asn Ser Glu Cys Ile Gln Cys His Pro Glu
545                 550                 555                 560
Cys Leu Pro Gln Ala Met Asn Ile Thr Cys Thr Gly Arg Gly Pro Asp
                565                 570                 575
Asn Cys Ile Gln Cys Ala His Tyr Ile Asp Gly Pro His Cys Val Lys
            580                 585                 590
Thr Cys Pro Ala Gly Val Met Gly Glu Asn Asn Thr Leu Val Trp Lys
        595                 600                 605
Tyr Ala Asp Ala Gly His Val Cys His Leu Cys His Pro Asn Cys Thr
    610                 615                 620
Tyr Gly Cys Thr Gly Pro Gly Leu Glu Gly Cys Pro Thr Asn Gly Pro
625                 630                 635                 640
Lys Ile Pro Ser Ile Ala Thr Gly Met Val Gly Ala Leu Leu Leu Leu
                645                 650                 655
Leu Val Val Ala Leu Gly Ile Gly Leu Phe Met Arg Arg Arg His Ile
            660                 665                 670
Val Arg Lys Arg Thr Leu Arg Arg Leu Leu Gln Glu Arg Glu Leu Val
        675                 680                 685
Glu Pro Leu Thr Pro Ser Gly Glu Ala Pro Asn Gln Ala Leu Leu Arg
    690                 695                 700
Ile Leu Lys Glu Thr Glu Phe Lys Lys Ile Lys Val Leu Gly Ser Gly
705                 710                 715                 720
Ala Phe Gly Thr Val Tyr Lys Gly Leu Trp Ile Pro Glu Gly Glu Lys
                725                 730                 735
Val Lys Ile Pro Val Ala Ile Lys Glu Leu Arg Glu Ala Thr Ser Pro
            740                 745                 750
Lys Ala Asn Lys Glu Ile Leu Asp Glu Ala Tyr Val Met Ala Ser Val
        755                 760                 765
Asp Asn Pro His Val Cys Arg Leu Leu Gly Ile Cys Leu Thr Ser Thr
    770                 775                 780
Val Gln Leu Ile Thr Gln Leu Met Pro Phe Gly Cys Leu Leu Asp Tyr
785                 790                 795                 800
Val Arg Glu His Lys Asp Asn Ile Gly Ser Gln Tyr Leu Leu Asn Trp
                805                 810                 815
Cys Val Gln Ile Ala Lys Gly Met Asn Tyr Leu Glu Asp Arg Arg Leu
            820                 825                 830
Val His Arg Asp Leu Ala Ala Arg Asn Val Leu Val Lys Thr Pro Gln
        835                 840                 845
His Val Lys Ile Thr Asp Phe Gly Leu Ala Lys Leu Leu Gly Ala Glu
    850                 855                 860
Glu Lys Glu Tyr His Ala Glu Gly Gly Lys Val Pro Ile Lys Trp Met
865                 870                 875                 880
Ala Leu Glu Ser Ile Leu His Arg Ile Tyr Thr His Gln Ser Asp Val
                885                 890                 895
Trp Ser Tyr Gly Val Thr Val Trp Glu Leu Met Thr Phe Gly Ser Lys
            900                 905                 910
Pro Tyr Asp Gly Ile Pro Ala Ser Glu Ile Ser Ser Ile Leu Glu Lys
        915                 920                 925
```

-continued

```
Gly Glu Arg Leu Pro Gln Pro Pro Ile Cys Thr Ile Asp Val Tyr Met
            930                 935                 940
Ile Met Val Lys Cys Trp Met Ile Asp Ala Asp Ser Arg Pro Lys Phe
945                 950                 955                 960
Arg Glu Leu Ile Ile Glu Phe Ser Lys Met Ala Arg Asp Pro Gln Arg
                965                 970                 975
Tyr Leu Val Ile Gln Gly Asp Glu Arg Met His Leu Pro Ser Pro Thr
            980                 985                 990
Asp Ser Asn Phe Tyr Arg Ala Leu Met Asp Glu Glu Asp Met Asp Asp
        995                 1000                1005
Val Val Asp Ala Asp Glu Tyr Leu Ile Pro Gln Gln Gly Phe Phe Ser
    1010                1015                1020
Ser Pro Ser Thr Ser Arg Thr Pro Leu Leu Ser Ser Leu Ser Ala Thr
1025                1030                1035                1040
Ser Asn Asn Ser Thr Val Ala Cys Ile Asp Arg Asn Gly Leu Gln Ser
                1045                1050                1055
Cys Pro Ile Lys Glu Asp Ser Phe Leu Gln Arg Tyr Ser Ser Asp Pro
            1060                1065                1070
Thr Gly Ala Leu Thr Glu Asp Ser Ile Asp Asp Thr Phe Leu Pro Val
            1075                1080                1085
Pro Glu Tyr Ile Asn Gln Ser Val Pro Lys Arg Pro Ala Gly Ser Val
        1090                1095                1100
Gln Asn Pro Val Tyr His Asn Gln Pro Leu Asn Pro Ala Pro Ser Arg
1105                1110                1115                1120
Asp Pro His Tyr Gln Asp Pro His Ser Thr Ala Val Gly Asn Pro Glu
                1125                1130                1135
Tyr Leu Asn Thr Val Gln Pro Thr Cys Val Asn Ser Thr Phe Asp Ser
            1140                1145                1150
Pro Ala His Trp Ala Gln Lys Gly Ser His Gln Ile Ser Leu Asp Asn
            1155                1160                1165
Pro Asp Tyr Gln Gln Asp Phe Phe Pro Lys Glu Ala Lys Pro Asn Gly
        1170                1175                1180
Ile Phe Lys Gly Ser Thr Ala Glu Asn Ala Glu Tyr Leu Arg Val Ala
1185                1190                1195                1200
Pro Gln Ser Ser Glu Phe Ile Gly Ala
            1205
```

Human EGFR
SEQ ID NO: 4

```
ccccggcgca gcgcggccgc agcagcctcc gccccccgca cggtgtgagc gcccgacgcg    60
gccgaggcgg ccggagtccc gagctagccc cggcggccgc cgccgcccag accggacgac   120
aggccacctc gtcggcgtcc gcccgagtcc ccgcctcgcc gccaacgcca caaccaccgc   180
gcacggcccc ctgactccgt ccagtattga tcgggagagc cggagcgagc tcttcgggga   240
gcagcgatgc gaccctccgg gacgccgggg cagcgctcc tggcgctgct ggctgcgctc   300
tgcccggcga gtcgggctct ggaggaaaag aaagtttgcc aaggcacgag taacaagctc   360
acgcagttgg cacttttga agatcatttt ctcagcctcc agaggatgtt caataactgt   420
gaggtggtcc ttgggaattt ggaaattacc tatgtgcaga ggaattatga tctttccttc   480
ttaaagacca tccaggaggt ggctggttat gtcctcattg ccctcaacac agtgagcga   540
attcctttgg aaaacctgca gatcatcaga ggaaatatgt actacgaaaa ttcctatgcc   600
ttagcagtct tatctaacta tgatgcaaat aaaaccggac tgaaggagct gcccatgaga   660
aatttacagg aaatcctgca tggcgccgtg cggttcagca caaccctgc cctgtgcaac   720
```

-continued

```
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080 gtgaacccg agggcaaata cagctttggt gccacctgcg tgaagaagtg tcccgtaat    1140 tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag cttggcctg aaaacaggac ggacctccat    1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg gacctccgg tcagaaaacc aaaattataa gcaacagagg tgaaaacagc    1740
tgcaaggcca caggccaggt ctgccatgcc ttgtgctccc ccgagggctg ctggggcccg   1800
gagcccaggg actgcgtctc ttgccggaat gtcagccgag gcaggaatg cgtggacaag   1860 tgcaaccttc tggagggtga gccaaggggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga tttggctg    2820 gccaaactgc tgggtgcgga agagaaagaa taccatgcag aaggaggcaa agtgcctatc   2880
aagtggatgg cattggaatc aatttttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctcctca gccacccata   3060 tgtaccatca atgtctacat gatcatggtc aagtgctgga tgatagacgc agatagtcgc   3120
ccaaagttcc gtgagttgat catcgaattc tccaaaatgg cccgagaccc ccagcgctac   3180
```

-continued

```
cttgtcattc aggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaatacta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt gcaacgtttt acaccgacta   4020
gccaggaagt acttccacct cgggcacatt ttgggaagtt gcattccttt gtcttcaaac   4080
tgtgaagcat ttacagaaac gcatccagca agaatattgt ccctttgagc agaaatttat   4140
cttcaaga ggtatatttg aaaaaaaaaa aagtatatg tgaggatttt tattgattgg   4200
ggatcttgga gtttttcatt gtcgctattg attttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca ataataact cggattccag cccacattgg attcatcagc   4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920
acccccaaa attagtttgt gttacttatg gaagatagtt ttctccttt acttcacttc   4980
aaaagctttt tactcaaaga gtatatgttc cctccaggtc agctgccccc aaaccccctc   5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgctttca caacatttgc   5220
agatgtttta gaaggaaaaa agttccttcc taaaataatt tctctacaat tggaagattg   5280
gaagattcag ctagttagga gcccacccttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaaatattt tcagcctaca gttatgttca   5460
gtcacacaca catacaaaat gttcctttg cttttaaagt aattttgac tcccagatca   5520
```

```
                                        -continued
gtcagagccc ctacagcatt gttaagaaag tatttgattt ttgtctcaat gaaaataaaa    5580
ctatattcat ttccactcta aaaaaaaaaa aaaaaa                              5616
```

Several EGFR mutations leading to constitutive activation have been associated with neoplastic growth and cancer progression in a variety of cancers, including lung cancer (in particular non-small cell lung carcinoma), head and neck cancer, ovarian cancer, cervical cancer, bladder cancer, and esophageal cancer (Nicholson et al., "EGFR and Cancer Prognosis," Eur J Cancer 37(4):9-15 (2001), which is hereby incorporated by reference in its entirety). Therefore, subjects suitable for EGFR mutational detection in accordance with methods of the present invention include subjects having any one of the aforementioned cancers.

A gain of function mutation suitable for detection in exosomal dsDNA samples in accordance with the present invention, includes, without limitation, the L858R mutation which results in leucine to arginine amino acid substitution at amino acid position 858 of human EGFR (SEQ ID NO: 3). This mutation occurs within the kinase domain (exon 21) and arises from a T>G nucleotide mutation at position 2573 of the EGFR gene sequence (SEQ ID NO: 4) (NCBI dbSNP reference SNP rs121434568; Mitsudomi et al., "Epidermal Growth Factor Receptor in Relation to Tumor Development: EGFR Gene and Cancer," FEBS J 277(2): 301-8 (2010), which are hereby incorporated by reference in their entirety).

Another gain of function mutation in EGFR suitable for detection in accordance with the present invention is the T790M mutation which results in a threonine to methionine mutation at amino acid position 790 in EGFR (SEQ ID NO: 3). This mutation occurs within the kinase domain (exon 20) and arises from a C>T mutation at nucleotide 2369 of the EGFR gene (SEQ ID NO: 4) (NCBI dbSNP reference SNP rs121434569; Tam et al., "Distinct Epidermal Growth Factor Receptor and KRAS Mutation Patterns in Non-Small Cell Lung Cancer Patients with Different Tobacco Exposure and Clinicopathologic Features," Clin Cancer Res 12:1647 (2006), which are hereby incorporated by reference in their entirety).

Another gain of function mutation in EGFR suitable for detection in accordance with the present invention is an in-frame deletion in exon 19. For example, deletions in amino acid residues 746-750, 746-751, 746-752, 747-751, 747-749, and 752-759 (SEQ ID NO: 3) have all been associated with lung cancer (see e.g., Mitsudomi et al., "Epidermal Growth Factor Receptor in Relation to Tumor Development: EGFR Gene and Cancer," FEBS J 277(2): 301-8 (2010), which is hereby incorporated by reference in its entirety). Detection of any one of these exon 19 deletions in exosomal dsDNA from a subject has prognostic/diagnostic and therapeutic implications in accordance with the present invention.

Subjects identified as having any of the above described EGFR mutations, or any other known EGFR mutations (i.e., insertions, deletions, duplications, etc), particularly gain-of-function mutations, are candidates for treatment using EGFR inhibitory agents which induce apoptosis and reduce proliferation of tumor growth (Ciardiello et al., "A Novel Approach in the Treatment of Cancer: Targeting the Epidermal Growth Factor Receptor," Clin Cancer Res 7:2958-2970 (2001); Ritter et al., "The Epidermal Growth Factor Receptor-Tyrosine Kinase: A Promising Therapeutic Target in Solid Tumors," Semin Oncol 30:3-11 (2003), which are hereby incorporated by reference in their entirety). Suitable EGFR inhibitors include, without limitation, small-molecule inhibitors of EGFR such as Gefitnib, Erlotinib (Tarceva), Afatinib (Gilotrif), Lapatinib (Tyverb) and monoclonal antibody inhibitors such as Panitumumab (Vectibix) and Cetuximab (Erbitux). Other EGFR inhibitors that are known in the art are also suitable for use in accordance with the methods of the present invention.

In another embodiment, the methods of the present invention involve contacting the isolated double-stranded DNA with one or more reagents suitable to quantify the amount of isolated double-stranded DNA from the recovered exosomes in the sample.

DNA can be quantified using any number of procedures, which are well-known in the art, the particular extraction procedure chosen based on the particular biological sample. For example, methods for extracting nucleic acids from urinary exosomes are described in Miranda et al. "Nucleic Acids within Urinary Exosomes/Microvesicles are Potential Biomarkers for Renal Disease," Kidney Int. 78:191-9 (2010) and in WO/2011/009104 to Russo, which are hereby incorporated by reference in their entirety. In some instances, with some techniques, it may also be possible to analyze the nucleic acid without extraction from the exosome.

In one embodiment, quantifying the amount of isolated double-stranded DNA is carried out by comparing the amount of isolated double-stranded DNA in a sample to that in a prior sample obtained from the selected subject.

The time between obtaining a first exosomal sample and a second, or any additional subsequent exosomal samples from a subject can be any desired period of time, for example, weeks, months, years, as determined is suitable by a physician and based on the characteristics of the primary tumor (tumor type, stage, location, etc.). In one embodiment of this aspect of the present invention, the first sample is obtained before treatment and the second sample is obtained after treatment. Alternatively, both samples can be obtained after one or more treatments; the second sample obtained at some point in time later than the first sample.

In another embodiment, quantifying the amount of isolated double-stranded DNA is carried out by comparing the amount of isolated double-stranded DNA to a standard. Exemplary standard exosomal samples are described supra. For example, the quantity of exosomal dsDNA obtained from B16F1 melanoma cells, H1975 and H1650 lung cancer cells, or U87 glioblastoma cells can serve as a standard sample that is indicative of the quantity of exosomal dsDNA associated with a low metastatic potential. Alternatively, the quantity of exosomal dsDNA obtained from B16F10 melanoma cells or Lewis lung carcinoma cells can serve as a standard sample that is indicative of the quantity of exosomal dsDNA associated with a high metastatic potential.

In a further embodiment, the methods of the present invention involve contacting the isolated double-stranded DNA with one or more reagents suitable to detect the methylation status of the DNA. DNA methylation involves the chemical addition of a methyl group to the 5' carbon position on the cytosine pyrimidine ring. Most DNA methylation occurs within CpG islands which are commonly found in the promoter region of a gene. Thus, this form of post modification of DNA acts as communicative signal for activation or inactivation of certain gene expression throughout various cell types. Methods to analyze DNA methylation status are well known in the art and include, but are not limited to, Me-DIP, HPLC, microarrays, and mass spectrometry. Another common method for DNA methylation analysis involves bisulfite treatment, in which unmethylated cytosines are converted to uracil while methylated cytosines remain unchanged, followed by downstream amplification and sequencing. The exosomal dsDNA methylation level or pattern can act as a surrogate for primary tumor cell status.

In yet another embodiment, the methods of the present invention involve contacting the isolated double-stranded DNA with one or more reagents suitable to quantify the amount of isolated double-stranded DNA able to enter a recipient cell.

DNA can be labeled using methods well known in the art including, but not limited to, use of various enzymes, prosthetic groups, fluorescent materials, luminescent materials, bioluminescent materials, and radioactive materials. The detectable substance may be coupled or conjugated either directly to the nucleic acid or indirectly, through an intermediate (such as, for example, a linker known in the art) using techniques known in the art. Examples of suitable enzymes include, but are not limited to, horseradish peroxidase, alkaline phosphatase, betagalactosidase, or acetylcholinesterase. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, Cascade Blue, rhodamine, dichlorotriazinylamine fluorescein, dansyl chloride, Texas Red, Oregon Green, cyanine (e.g., CY2, CY3, and CY5), allophycocyanine or phycoerythrin. An example of a luminescent material includes luminol. Examples of bioluminescent materials include, but are not limited to, luciferase, luciferin, green fluorescent protein (GFP), enhanced GFP (Yang et al., 1996), and aequorin. Once the exosomal dsDNA is labeled (e.g., by either BrdU or EdU), it is contacted with a preparation of suitable recipient cells, and the amount of dsDNA that enters the recipient cells is imaged and quantified using well known microscopy techniques, such as atomic force microscopy, electron microscopy, and advanced confocal microscopy. For electron microscopy, immunogold-labeling of dsDNA may be employed. Suitable recipient cells include, but are not limited to, fibroblasts, bone marrow cells, epithelial cells, and macrophages. For prognostic purposes, a high quantity of exosomal dsDNA able to enter a recipient cell is indicative of a poorer prognosis and higher metastatic potential. A low quantity of exosomal dsDNA able to enter a recipient cell is indicative of a good prognosis and lower metastatic potential.

EXAMPLES

The examples below are intended to exemplify the practice of the present invention but are by no means intended to limit the scope thereof.

Materials and Methods for Examples 1-5

Cell Lines and Cell Culture.

B16-F10, B16-F1, B16-F0, 67NR, 4T1, MDA-MB-231, MDA-MB-1833, MDA-MB-4175, LLC, HCT-116 (Horizon Discovery), PANC1 and AsPc1 cells were cultured in DMEM, and human melanoma cells (SK-Mel-, A375M and A375P), as well as Pan02, Pan02-H3, PanCaco, BXPC-3, HPAF-II, EO771, H292, H1975, H1650, K-562 (DSMZ), 22RV and HL-60 cells were cultured in RPMI supplemented with penicillin (100 U ml$^{-1}$) and streptomycin (100 pg ml$^{-1}$) and 10% exosome-depleted FBS. Cell lines were obtained from American Type Culture Collection if not otherwise mentioned. Human melanoma cell lines were obtained from Memorial Sloan-Kettering Cancer Center (MSKCC).

Animal Models and Plasma Collection.

C57BL/6 and NOD/SCID mice were obtained from Jackson Laboratory and maintained at the Weill Cornell Medical College (WCMC) animal facility. All procedures were performed according to protocols approved by the Institutional Animal Care and Use Committee of WCMC and MSKCC.

To analyze the circulating exoDNA from melanoma-bearing mice, NOD/SCID mice were subcutaneously implanted with 2×10$^6$ human melanoma SK-Mel28 cells mixed with an equal volume of matrigel (BD Biosciences). Mice were sacrificed when the tumor reached maximum size allowed by the IACUC protocol and peripheral blood was obtained by retro-orbital bleeding directly into anti-coagulant tubes (EDTA). Plasma was separated from blood cells by sequential centrifugation at 500×g for 10 min followed by 3000×g for 10 min, and subjected to exosome isolation as described below.

Exosome Preparation and exoDNA Extraction.

Exosomes were prepared using differential ultracentrifugation methods essentially as described before (Peinado et al., "Melanoma Exosomes Educate Bone Marrow Progenitor Cells Toward a Pro-metastatic Phenotype Through MET," *Nature Medicine* 18:883-891 (2012), which is hereby incorporated by reference in its entirety), and resuspended in PBS for subsequent analysis. For mouse plasma samples, the plasma was filtered through a 1.2 µm membrane to remove debris and large particles, then subjected to ultracentrifugation to pellet and wash exosomes. DNA was extracted from exosomes using the QIAamp DNA mini kit (QIAGEN) following the manufacturer's protocol and eluted with 50 l of 10 mM Tris pH8.0. DNA quality and quantity were analyzed using Nanodrop and Agilent Bioanalyzer chips.

DNase Digestion Analysis of exoDNA.

Approximately 40 micrograms of purified exosomes resuspended in PBS were treated either with S1 nuclease (Fermentas) or dsDNA-specific Shrimp DNase (Fermentas and Affymetrix). Equal amounts of exosomes were used as untreated controls. The digestion was performed at 30 degrees Celsius for 30 minutes for S1 nuclease and Shrimp dsDNase (Affymetrix). While using Shrimp dsDNase (Fermentas) the digestion was performed at 37 degrees Celsius for 30 min. Reaction mixtures were prepared according to manufacturers recommendations. After digestion the enzymes were heat inactivated at 70 degrees Celsius for five minutes in presence of EDTA according to manufacturer's instructions. Exosomal DNA was extracted using QIAamp DNA mini kit (Qiagen) and the eluted DNA was distributed equally and further subjected to S1 nuclease or Shrimp dsDNase treatment. All digestions were set up in 20 microliters reaction and after digestion 15 microliters of each sample resuspended in 1×DNA loading dye, (Fermentas) along with 1 kb DNA ladder (Fermentas) were loaded on a 1.5% agarose gel (Ultrapure agarose from Invitrogen) run at 150 V for 45 mins. The agarose gel was stained with SyBrGreen gold (1:5000 dilution in 1×TAE) for 45 minutes and imaged with Spectroline UV transilluminator (Kodak).

For detection of dsDNA using QuantiFluor® dsDNA System (Promega), 5 microliters of the digested or undigested mixes was mixed with QuantiFluor® dsDNA specific fluorescent dye and quantification of DNA was performed using manufactures protocol. The fluorescent intensity was measured using Spectramax M5 from Molecular devices.

Whole Genome Sequencing, CGH Array and Bioinformatics Analysis.

1 μg of each exoDNA and gDNA sample was subjected to Illumina TruSeq library preparation and High Throughput DNA sequencing following manufacture's instruction. Short reads were aligned to the reference mouse genome (mm9) using the BWA computer programs with default parameters. Clonal reads were collapsed using custom scripts. Aligned read densities across the entire genome were then calculated using 100 Kb bins and represented using Circos plots.

For the CGH assay, exoDNA and gDNA samples were labeled using the Genomic DNA Enzymatic Labeling Kit (Agilent Technologies) following manufacture's instruction, and two color hybridization was performed using SurePrint G3 and HD CGH microarrays purchased from Agilent Technologies following standard procedures. The arrays were then analyzed and copy number visualized using the Agilent Genomic Workbench software analysis tools.

Dot Blot.

DNA samples were denatured with 0.4N NaOH at room temperature for 30 min, then placed on ice immediately and neutralized with an equal volume of pre-cooled 0.95M Tris (pH6.8) buffer. A four-fold serial dilution of exoDNA starting at 200 ng was dot blotted on Nylon membrane and crosslinked in a Stratalinker. The membranes were blocked with TBST buffer containing 1% milk and then probed with anti-5'-methylcytidine (Eurogentec) and anti-DNA (American Research Products, Inc) antibodies and developed with SuperSignal West Femto Chemiluminescent reagent (Thermo Scientific).

Transmission Electron Microscopy.

Exosome samples were fixed in 2% paraformaldehye and 0.2% glutaraldehyde in 0.1 M phosphate buffered saline and centrifuged to form a 1 mm thick visible pellet on the wall of a microcentrifuge tube. The pelleted exosomes were rinsed without resuspension in 0.5% sodium borohydride to block aldehyde groups and then dehydrated in a graded series of ethanol before being infiltrated in 100% LR White resin for 18 hours at 4° C. All the processing was done in the same microcentrifuge tube and solutions were changed so as not to disturb the exosome pellet. The resin was polymerized at 60° C. overnight and the microcentrifuge tube was cut away so that the exosomes could be thin sectioned. 100 nm thick sections were collected on nickel grids. Post embedding immunogold labeling was done for DNA labeling using the mouse monoclonal antibody AC-30-10 (EMD Millipore, Billerica, Mass. 01821 USA) and 10 colloidal gold conjugated to goat anti mouse IgM secondary antibodies were used to reveal the presence of DNA (BB International, Ted Pella Redding Calif. 96049 USA). Positive control sections consisted of sections of LR white embedded human bone marrow; negative control sections were incubated in secondary antibody without being exposed to primary antibody. Following immunogold labeling, sections were counterstained with 1% uranyl acetate and then examined in a Hitachi H7000 electron microscope at 75 kV accelerating voltage. Images were collected on Kodak 4489 film and after development were scanned at 2400 DPI and the images were processed for contrast using Adobe Photoshop.

Mutational Analysis of BRAF and EGFR.

To detect mutations in BRAF and EGFR genes, AS-PCR assays were adopted and modified from literature (Dahse et al., "Two Allele-specific PCR Assays for Screening Epidermal Growth Factor Receptor Gene Hotspot Mutations in Lung Adenocarcinoma," *Molecular Medicine Reports* 1:45-50 (2008); Jarry et al., "Real-time Allele-specific Amplification for Sensitive Detection of the BRAF Mutation V600E," *Molecular and Cellular Probes* 18:349-352 (2004); Uhara et al., "Simple Polymerase Chain Reaction for the Detection of Mutations and Deletions in the Epidermal Growth Factor Receptor Gene: Applications of This Method for the Diagnosis of Non-small-cell Lung Cancer," *Clinica Chimica Acta; International Journal of Clinical Chemistry* 401:6872 (2009), which are hereby incorporated by reference in their entirety). In brief, for both BRAF V600E and EGFR T790M mutations, standard PCR reactions containing 1.5 mM MgCl2 and primer pairs either for wild-type or mutant alleles at 0.5 M for BRAF and 2.5 M for EGFR were used, respectively. The PCR programs are the following: 95° C., 5 min; 40 cycles of (95° C., 5 sec, 66° C. (BRAF)/56° C. (EGFR), 5 sec and 72° C., 5 sec); 72° C., 5 min. For detection of Exon 19 deletion in EGFR, PCR reactions containing 1.5 mM MgCl2 and each of the four primers at 0.25 M were conducted. The PCR program is as follows: 95° C., 5 min; 40 cycles of (95° C., 30 sec, 58° C., 30 sec and 72° C., 30 sec); 72° C., 5 min. A higher cycle number (80) was used when assessing the sensitivity of the assay and when circulating exoDNA was analyzed. End point PCR products were analyzed by agarose gel (2%) electrophoresis.

Brdu-Labeling of exoDNA and Transferring Assays.

B16-F10 cells were incubated with 10 mM BrdU for 24 h and washed with PBS. Fresh DMEM media supplemented with exosome-depleted fetal bovine serum was added to the cells and cells were cultured for another 24 h. The supernatant was then harvested for exosome preparation. For in vitro exoDNA transfer assays, NIH3T3 cells or freshly isolated lineage-negative bone marrow cells were treated with BrdU-labeled vs. non-labeled B16-F10 exosomes at 10 g/ml for 24 h, then cells were fixed directly or cytospun on coverslips followed by fixation with 4% paraformaldehyde and immunofluorescence staining with anti-BrdU antibody (Invitrogen). For in vivo studies, 10 g of BrdU-labeled or non-labeled B16-F10 exosomes in a total volume of 150 μl PBS were administrated into C57BL/6 mice via tail vein injection, and 24 h later the mice were sacrificed and blood and whole bone marrow samples were processed as described by Peinado et al., "Melanoma Exosomes Educate Bone Marrow Progenitor Cells Toward a Pro-metastatic Phenotype Through MET," *Nature Medicine* 18:883-891 (2012), which is hereby incorporated by reference in its entirety, and analyzed with APC-BrdU flow kit (BD Pharmingen) following manufacturer's instructions. As positive controls, freshly isolated whole bone marrow cells were either treated directly with 10 mM BrdU for 30 min or with 10 g of BrdU-labeled or non-labeled B16-F10 exosomes for 16 h and then analyzed with APC-BrdU flow kit.

Example 1—Double-Stranded DNA (dsDNA) is Present in Exosomes Derived from Various Cancer Cell Types Previous studies have demonstrated that proteins and genetic material such as mRNAs and miRNAs can be selectively packaged into exosomes in a cell type-dependent manner (Valadi et al., "Exosome-mediated Transfer of mRNAs and microRNAs is a Novel Mechanism of Genetic Exchange Between Cells," *Nature Cell Biology* 9:654-659 (2007), which is hereby incorporated by reference in its entirety). This is the first report providing evidence for the presence of dsDNA inside exosomes derived from multiple cancer cell lines: human K-562 chronic myeloid leukemia cells (FIG. 1A), human HCT116 colorectal carcinoma cells (FIG. 1B), and murine B16-F10 (highly metastatic) melanoma cells (FIG. 1C). To carefully characterize exosomal DNA within exosomes, extracellular and non-specific DNA present on the exosomal surface was eradicated using ssDNA-specific S1 Nuclease or dsDNA specific Shrimp DNase. Further to determine the nature of DNA present inside exosomes, the combination of S1 nuclease and dsDNase enzymes was used again to selectively digest single-stranded versus double-stranded DNA. It was observed that dsDNA-specific Shrimp DNase completely degraded the DNA associated with exosomes derived from all three cell sources included in the study. Moreover, it was observed that the size of the major population of dsDNA inside the exosomes ranged between 100 bp to 2500 bp whereas the population of dsDNA outside the exosomes constituted DNA species greater than 2500 bp in size. As a control, it was shown that Shrimp dsDNase completely degraded the genomic DNA (FIG. 1A, Lane 13).

Figure 2A:
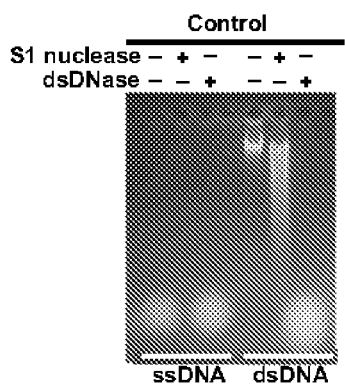
FIGS. 2A-2B shows the specificity of S1 nuclease and shrimp DNase.

To validate the specificity of the S1 nuclease and shrimp dsDNase, gDNA, purified ssDNA oligonucleotides and lamda dsDNA were included as controls in the study (FIG. 2A).

Figure 2B:
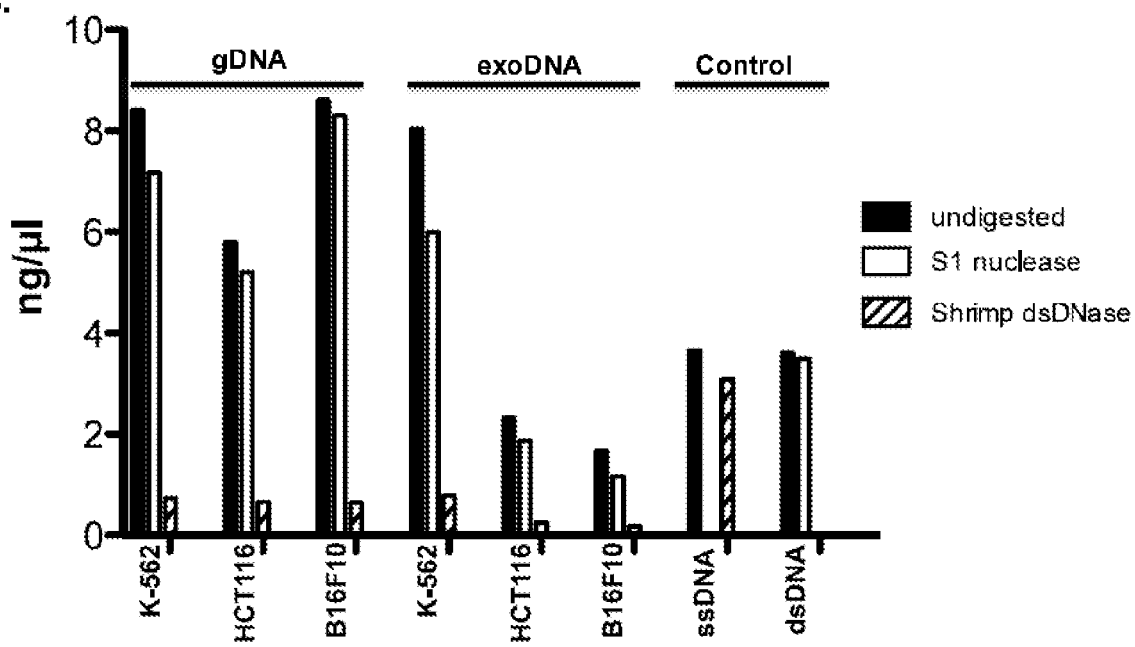

Next, to quantify exosomal dsDNA, the QuantiFluor® dsDNA System (Promega) was used which employs a dsDNA-specific fluorescent DNA-binding dye and enables sensitive quantitation of small amounts of double-stranded DNA (dsDNA) in solution. In contrast to undigested or S1 nuclease-treated exosomes, a strong reduction in the binding of dsDNA-specific fluorescent DNA-binding dye in the samples was obtained where exoDNA was treated with shrimp dsDNase (FIG. 2B). This result further confirms the finding that the majority of DNA associated with exosomes is indeed double-stranded in nature.

Figure 3:
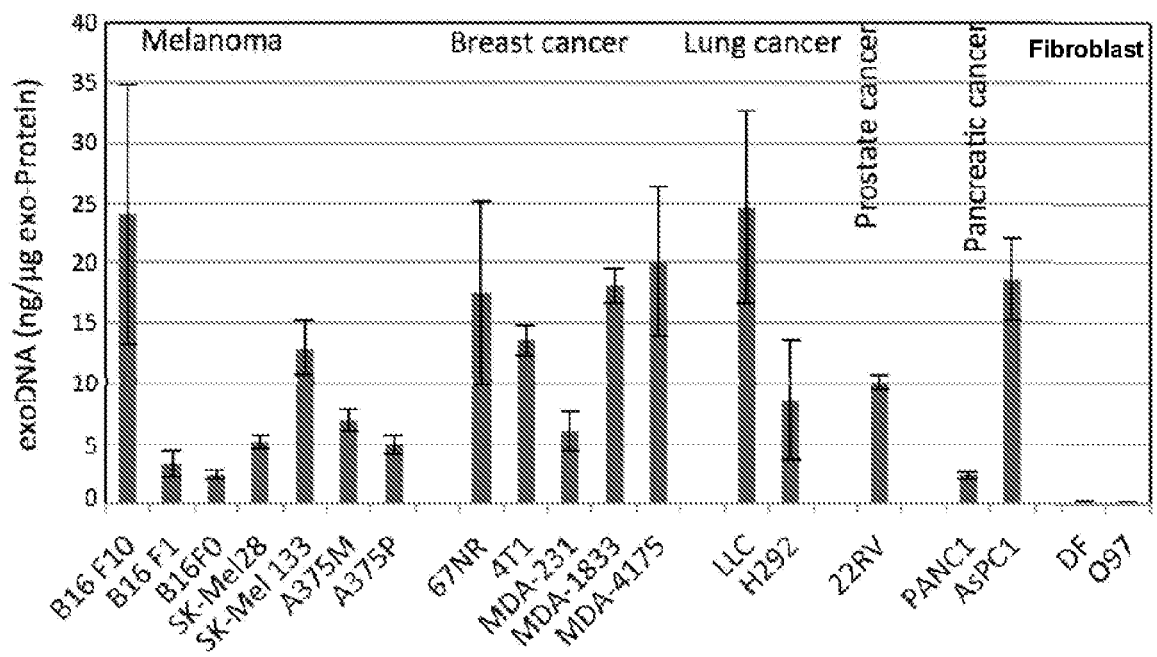
FIG. 3 shows DNA is present in tumor-cell derived exosomes. DNA was extracted from exosomes secreted by different types of cancer cell lines including melanoma (B16-F10, B16-F1, B16-FO, SK-Mel28, SK-MEL133, A375M and A375P), breast cancer (67NR, 4T1, MDA-MB-231, MDA-MB-1833 and MDA-MB-4175), lung cancer (LLC and H292), prostate cancer (22RV1), and pancreatic cancer (PANC1 and AsPC1). DNA abundance was expressed as "nanogram of DNA per microgram of exoProtein". DNA abundance was also evaluated for exosomes derived from two healthy human primary stromal fibroblast cell lines, DF and 097. Experiments were performed in duplication and results are shown as mean±standard errors (n=2).

To determine whether the association of DNA with exosomes is a common feature of cancer cells, the analysis of exoDNA was extended to a broader range of cancer types. As shown in FIG. 3, exoDNA was detected at various levels in a panel of cancer cell lines including melanoma, breast cancer, lung cancer, prostate cancer, and pancreatic cancer. Furthermore, whether DNA is present in exosomes derived from normal stromal cells, such as fibroblasts (FIG. 3), was investigated. Although exoDNA could be isolated from exosomes derived from human dermal fibroblasts and human mammary tissue-derived fibroblasts, there was ~20-fold less DNA in these exosomes compared to exosomes isolated from tumor cells (FIG. 3). Therefore, the abundance of exoDNA varies depending on cell type, with tumor-derived exosomes containing considerably more DNA than exosomes isolated from normal cells. Next, to understand the nature of DNA inside the exosomes, some of the cancer cell lines used in FIG. 3 were selected. After eradication of the external exoDNA by using method mentioned earlier in FIG. 1A-C, it is demonstrated that in almost all cancer cell lines the majority of DNA inside the exosomes is double-stranded in nature (FIG. 1D).

Figure 4:
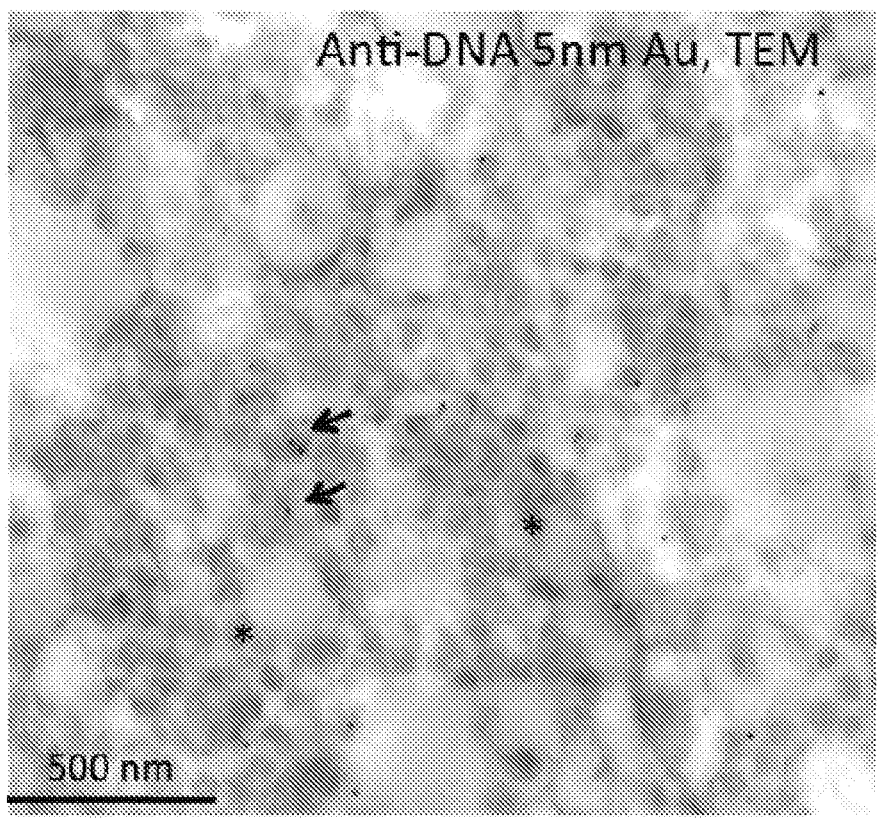
FIG. 4 shows detection of DNA in exosomes by immunogold electron microscopy. B16F10 exosome pellets were subjected to immunogold electron microscopy analysis using an anti-DNA antibody. The small grey areas represent exosomes (*) and the solid black dots represent the DNA (arrow).

To further validate the presence of DNA in exosomes, and to determine its distribution in the population of exosomes, immunogold electron microscopy of exosomes derived from murine B16-F10 melanoma was performed using an anti-DNA antibody (FIG. 4). Interestingly, this study revealed that only a subset of exosomes indeed contained DNA (roughly ~10% of B16-F10 exosomes).

Figure 5A:
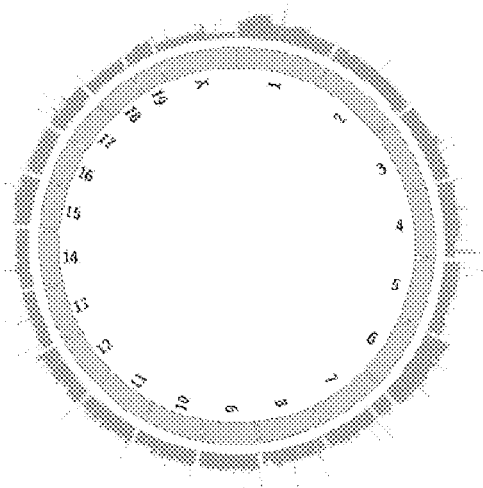
FIGS. 5A-5B show exoDNA represents genomic DNA and phenocopies mutational status of parental tumor cells.
Figure 5B:
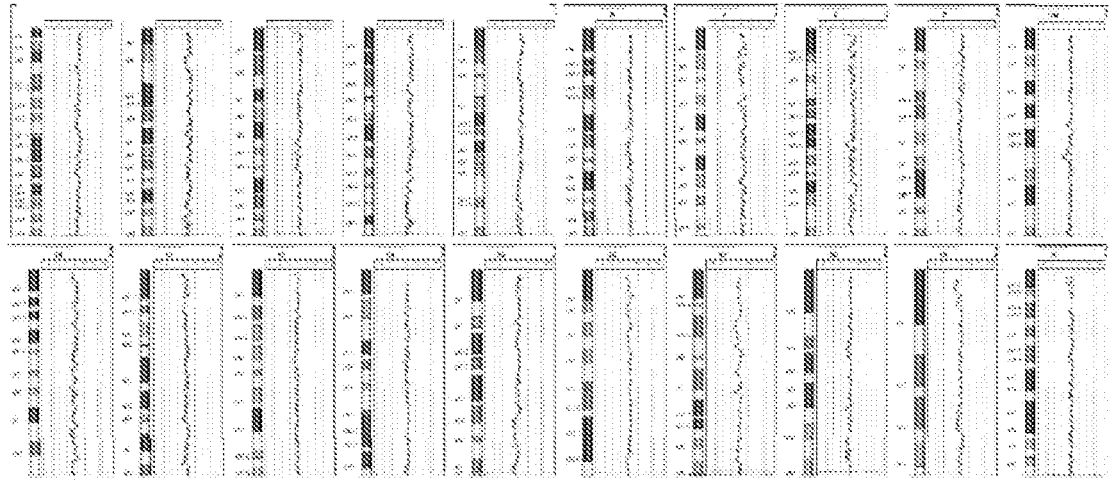

Example 2—Exosomal DNA Represents the Entire Genomic DNA of Parental Tumor Cells To determine if the genetic abnormalities driving tumorigenesis in cancer cells are represented and can be detected in exoDNA, both high throughput whole genome sequencing (FIG. 5A) and comparative genomic hybridization (CGH) analysis (FIG. 5B) were first carried out to examine, in an unbiased manner, the genome coverage of exoDNA. These analyses revealed that total genomic DNA (but not mitochondrial DNA) was represented in exoDNA. No bias for gene-coding versus intergenic regions and sense versus antisense strands of gene-coding regions was observed in the exoDNA. In addition, no specific fragments were highly enriched or depleted in the exoDNA pool compared to the genomic DNA.

Figure 6:
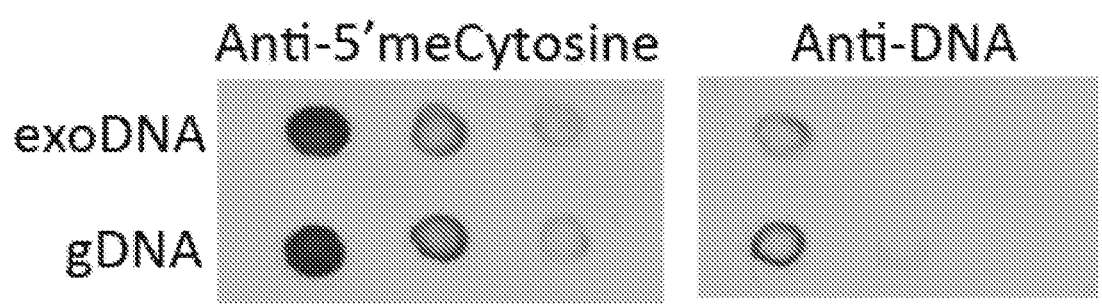
FIG. 6 shows exoDNA methylation levels are comparable to those of gDNA. Dot blotted DNA was probed with an anti-5' methyl-Cytosine antibody to determine the cytosine methylation level of exoDNA vs. gDNA. Probing of the same blot with anti-DNA antibody serves as a loading control.

In intact cells, 5'-cytosine methylation is a major modification of nuclear DNA involved in various biological processes, such as transcription and DNA repair. Therefore, the overall level of 5'-cytosine methylation of exoDNA was examined. It was found that, much like nuclear genomic DNA, exoDNA is also methylated, and to a level similar to that of cellular DNA (FIG. 6).

Figure 7A:
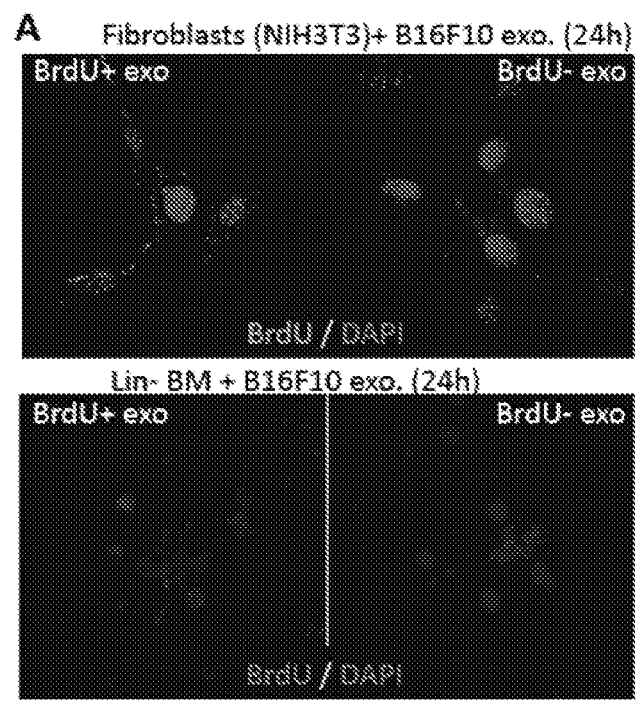
FIGS. 7A-7B show exoDNA can be horizontally transferred to different cell types in vitro and in vivo.
Figure 7B:
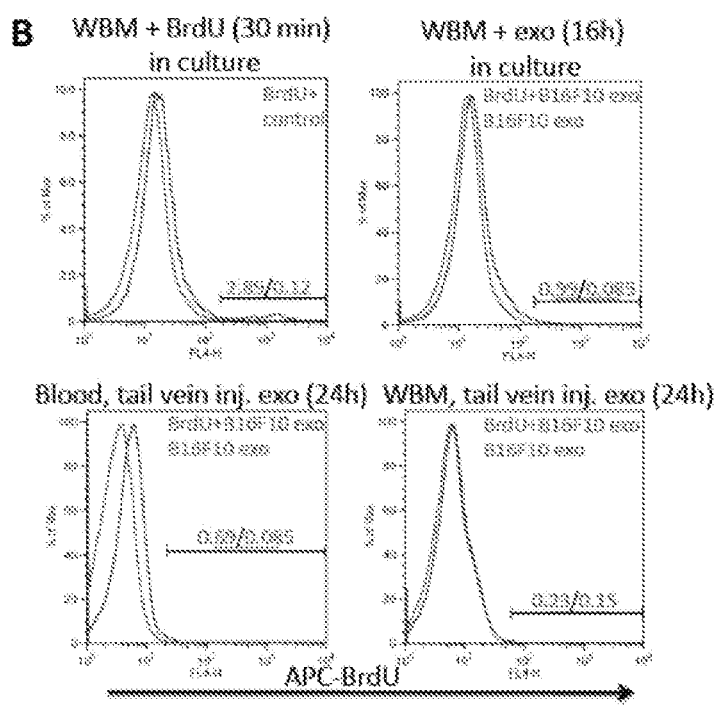

Example 3—Horizontal Transfer of Exosomal DNA from Donor Cells to Recipient Cells It is now widely accepted that exosomes can mediate the horizontal transfer of functional molecules, such as oncogenic proteins, membrane-bound tyrosine kinase receptors and mRNAs of angiogenic factors, into target cells, resulting in epigenetic reprogramming of these recipient cells, and therefore, initiating profound biological responses (Peinado et al., "Melanoma Exosomes Educate Bone Marrow Progenitor Cells Toward a Pro-metastatic Phenotype Through MET," *Nature Medicine* 18:883-891 (2012); Zhang et al., "Exosomes and Immune Surveillance of Neoplastic Lesions: a Review," *Biotech. Histochem.* 87:161-168 (2012), which are hereby incorporated by reference in their entirety). However, there have been no reports investigating the transfer of exoDNA from donor to recipient cells. Therefore, whether exoDNA can be horizontally transferred into other cells was determined. First, exosomes were isolated from BrdU-labeled B16F10 cells, and it was confirmed that the exoDNA was indeed BrdU+. This approach allowed tracking of exoDNA in subsequent assays. The uptake of exoDNA by fibroblast (NIH3T3) or lineage negative bone marrow cells by immunofluorescence microscopy was then examined 24 hours post treatment of these cells with BrdU-labeled exosomes. BrdU-labeled exoDNA was clearly detected in the treated cells (FIG. 7A), and it was observed that, at this time point post exosome-treatment, the majority of exoDNA is localized in the cytoplasm of treated cells. Furthermore, using a similar approach followed by flow cytometric detection of BrdU, it was demonstrated that BrdU+ exoDNA from B16-F10 melanoma exosomes injected intravenously in mice was transferred to blood and bone marrow cells (FIG. 7B). Therefore, exoDNA is uptaken by various recipient cell types both in vitro and in vivo.

Figure 8:
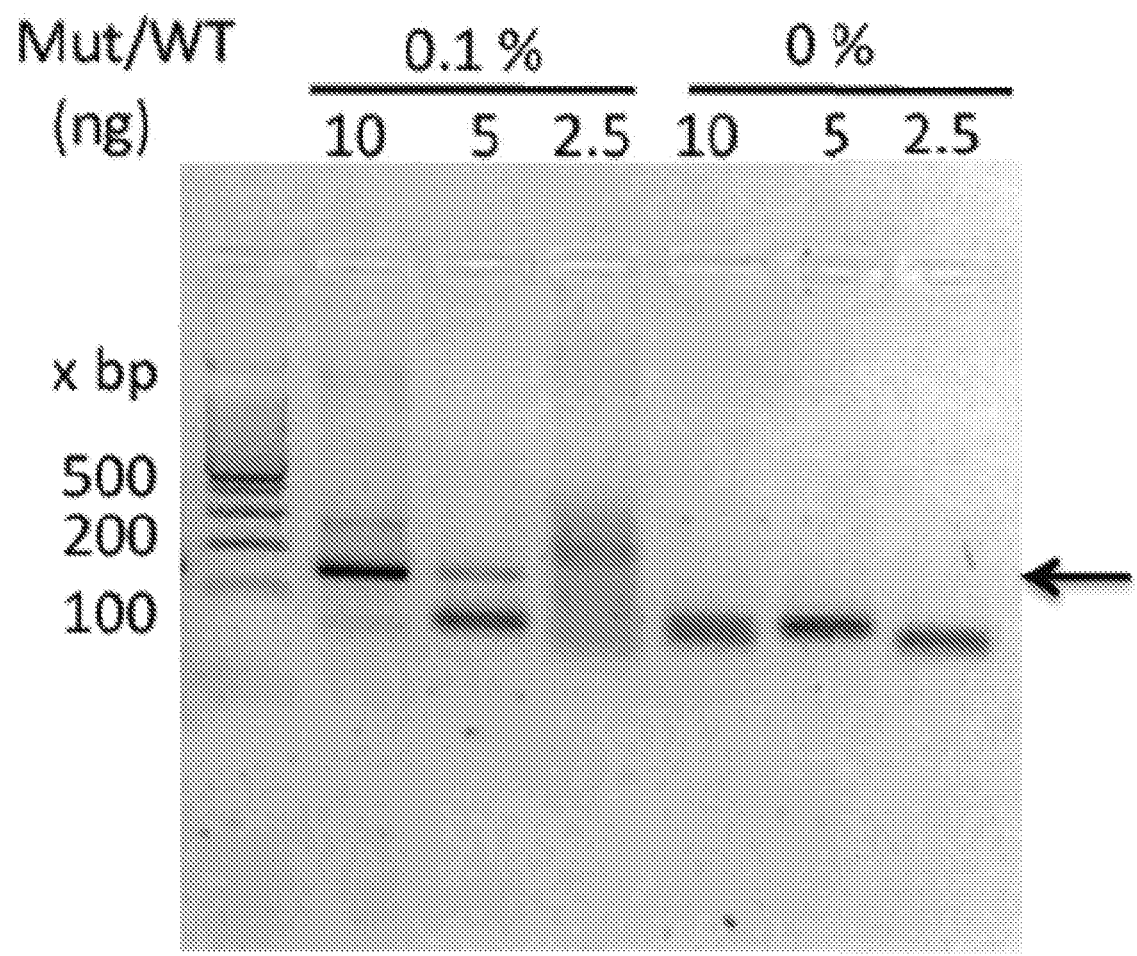
FIG. 8 shows evaluation of the sensitivity and specificity of AS-PCR assay for BRAF(V600E) mutation detection. Genomic DNA containing no BRAF(V600E) mutation or 0.1% of this mutation were used as template for AS-PCR to assess the sensitivity and specificity of the assay. Different amounts of template DNA (as low as 2.5 ng) were examined.
Figures 9A, 9B:
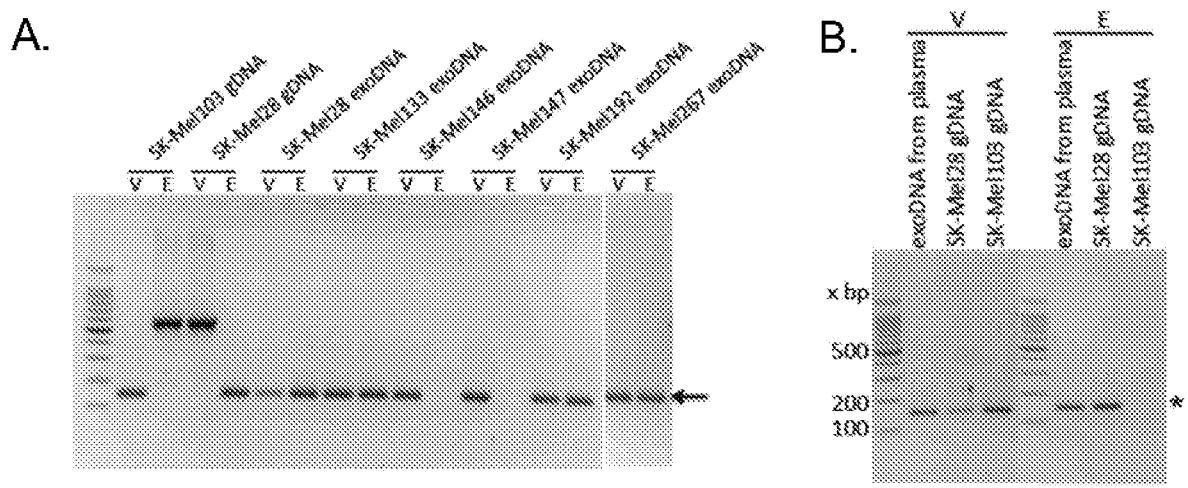
FIGS. 9A-9B show detection of BRAF V600E mutation.

Example 4—Exosomal DNA Phenocopies the Mutational Status of the Parental Tumor Cells The finding that exoDNA represents genomic DNA, and that it can be easily detected in purified exosomes prompted the examination of whether exoDNA could be utilized as a surrogate for tumor tissues or cells to detect tumor-specific genetic mutations. To this end, DNA isolated from exosomes derived from various cancer cell lines was tested, including melanoma and lung cancer for driver mutations known to be present in those cell lines. Since the BRAF (V600E) mutation is present in 50% of malignant melanomas (Daniotti et al., "Cutaneous Melanoma in Childhood and Adolescence Shows Frequent Loss of INK4A and Gain of KIT," *The Journal of Investigative Dermatology* 129:1759-1768 (2009); Davies et al., "Mutations of the BRAF Gene in Human Cancer," *Nature* 417:949-954 (2002); Gorden et al., "Analysis of BRAF and N-RAS Mutations in Metastatic Melanoma Tissues," *Cancer Research* 63:3955-3957 (2003), which are hereby incorporated by reference in their entirety), allele-specific polymerase chain reaction (AS-PCR) analysis was performed (adopted and modified from Jarry et al., "Real-time Allele-specific Amplification for Sensitive Detection of the BRAF Mutation V600E," *Molecular and Cellular Probes* 18:349-352 (2004), which is hereby incorporated by reference in its entirety) to evaluate the mutational status of BRAF in exoDNA isolated from several human primary melanoma cell lines which harbor either wild type (WT; SK-Mel146 and SK-Mel 147) or mutated BRAF (SK-Mel 28, SK-Mel 133, SK-Mel 192, and SK-Mel 267). First, proof of principle experiments were performed to verify the sensitivity and specificity of the AS-PCR assay (FIG. 8). Using primers that distinguished between wild type ("V") and mutant alleles ("E") of BRAF, the mutant allele could be detected in exoDNA of all cell lines containing the mutation, whereas only the wild-type allele was detected in those cell lines with non-mutated BRAF (FIG. 9A). These findings demonstrated that exoDNA reflects the mutational BRAF status of the parental cell lines.

Figure 10:
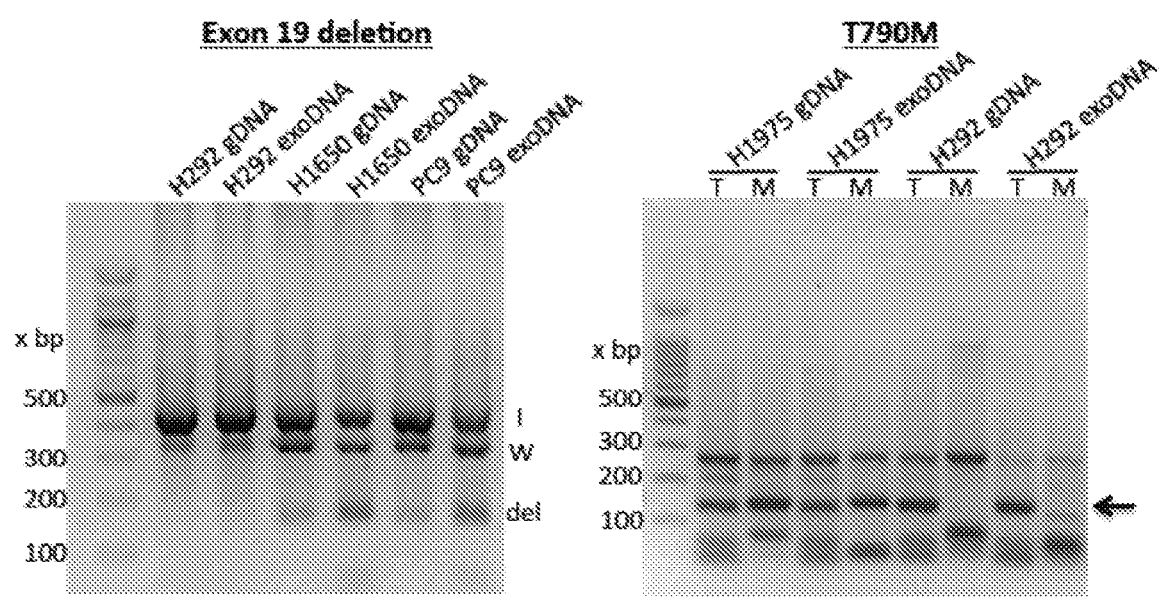
FIG. 10 shows detection of EGFR mutations in exoDNA isolated from lung cancer cells. gDNA and exoDNA were extracted from human non-small cell lung cancer (NSCLC) cell lines harboring WT (H292), exon 19 deletion (H1650 and PC9), and T790M mutation (H1975) of EGFR. AS-PCR was employed to detect WT and mutant alleles. For deletion of exon 19 mutation, "I" indicates internal control; "W", wild type; and "del", deletion of exon 19. For T790M mutation, "T" indicates wild type allele, and "M" indicates the mutant allele. The arrow marks the expected size of PCR products.
Figures 11A, 11B, 11C, 11D:
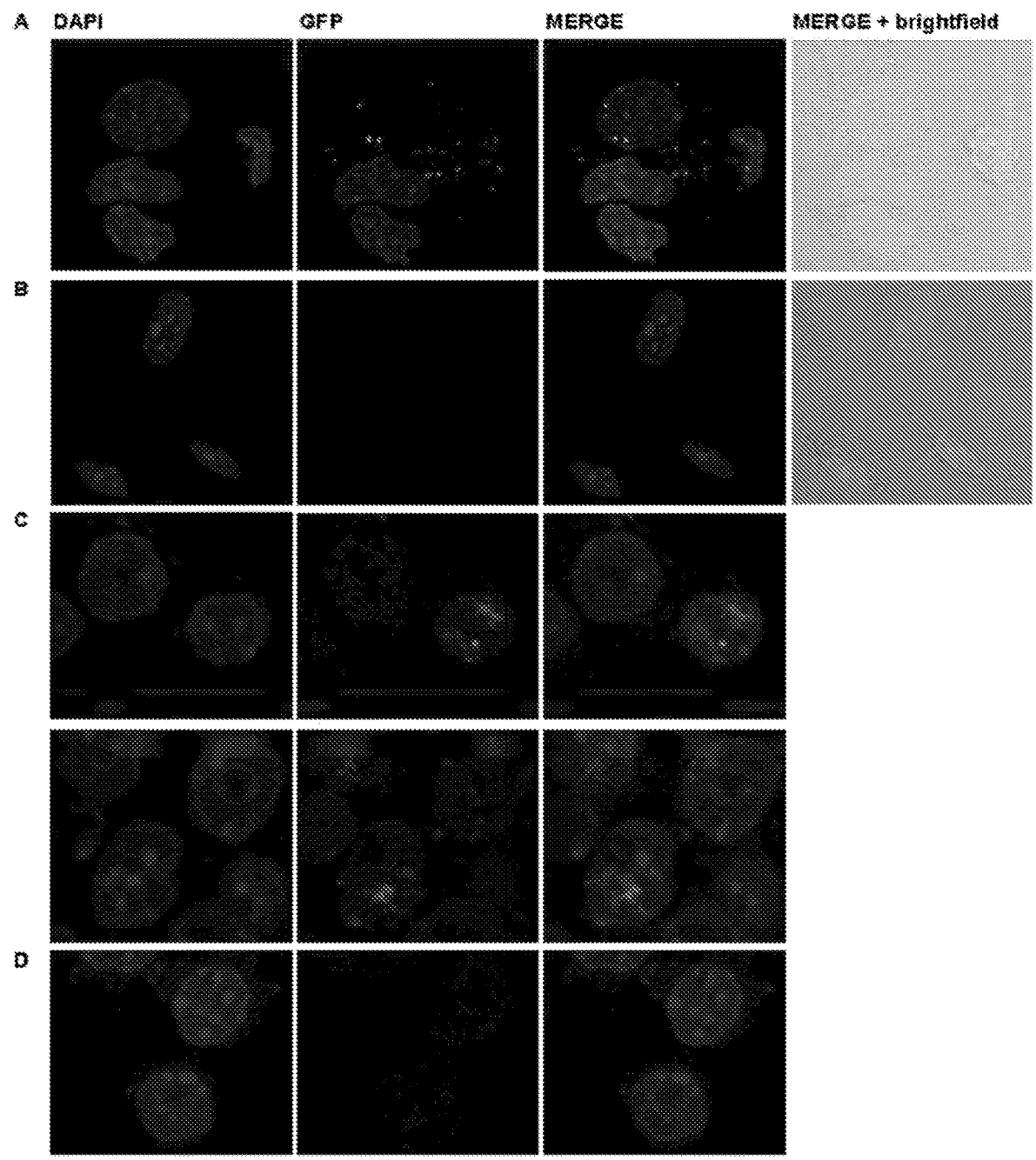
FIGS. 11A-11D show double-stranded exoDNA entering the nucleus of recipient cells.

A second example of a well-described tumor-associated mutation is the epidermal growth factor receptor (EGFR), which is mutated in several types of cancers, including non-small cell lung cancer (NSCLC) (Lynch et al., "Activating Mutations in the Epidermal Growth Factor Receptor Underlying Responsiveness of Non-small-cell Lung Cancer to Gefitinib," *The New England Journal of Medicine* 350: 2129-2139 (2004); Paez et al., "EGFR Mutations in Lung Cancer: Correlation with Clinical Response to Gefitinib Therapy," *Science* 304:1497-1500 (2004); Pao et al., "EGF Receptor Gene Mutations are Common in Lung Cancers from "Never Smokers" and are Associated with Sensitivity of Tumors to Gefitinib and Erlotinib," *Proceedings of the National Academy of Sciences of the United States of America* 101:13306-13311 (2004), which are hereby incorporated by reference in their entirety). Gain-of-function mutations within the kinase domain of EGFR, such as the L858R point mutation, a deletion in 19 exon (19Del), and the T790M gate-keeper mutation, are crucial for selecting those patients who will benefit from targeted therapy using tyrosine kinase inhibitors. AS-PCR was again employed to assess exosomal DNA from several NSCLC cell lines, including the H292 cell line (wildtype), the H1975 cell line (harboring the L858R and T790M point mutations), and the H1650 and PC9 cell lines (harboring the exon 19 deletion). EGFR mutations were detected in 100% of exoDNA isolated from cultured NSCLC cell lines having these known EGFR mutations as shown in FIG. 10.

Example 5—Mutational Analysis of Exosomal DNA in Cell Line and Clinical Samples of Non-Small Cell Lung Cancer Numerous studies have demonstrated that tumor cells secrete exosomes into the peripheral circulation and that these exosomes, which can be obtained non-invasively using a simple blood test, represent a reservoir of biomarkers. To assess the feasibility of detecting tumor-associated genetic mutations in circulating exoDNA a preclinical animal model of melanoma was employed. Specifically, human melanoma cells (Sk-Mel 28) harboring the BRAF(V600E) mutation were subcutaneously implanted in the flanks of NOD/SCID mice. Plasma was harvested when the tumor reached the size limit allowed by the standard animal protocol. Circulating exosomes were isolated using ultracentrifugation procedure, and dsDNA from within the exosomes was extracted and assayed for the BRAF(V600E) mutation. As demonstrated in FIG. 9B, the V600E mutation was present in the circulating exoDNA isolated from melanoma-bearing mice, suggesting that this assay could be translated to the clinic.

Example 6—Exosomal DNA Enters the Nucleus of Recipient Cells

To investigate exosome and exo-DNA transfer upon education of mouse bone marrow and RAW 264.7 target cells, exosomes from B16-F10 mouse melanoma cell line were collected in the presence or absence of EdU (10 μg/ml; Invitrogen; Click-it EdU Imaging Kit) in the cell culture medium for 72 hrs. By using a purification protocol including ultracentrifugation of exosomes in a sucrose cushion layer, homogenous populations of exosomes were obtained. Mouse bone marrow and RAW 264.7 cells were seeded in 24-well plates (bone marrow: $0.5 \times 10^6$/well; RAW: 10,000/well in 500 ml growth media overnight). The following day, media was replaced with fresh media containing exosome depleted FBS and cells were incubated with 20 μg/ml of either unlabeled or EdU labeled exosomes. After 48 hours of incubation, cells were fixed (3.7% paraformaldehyde) and permeabilized (0.5% Triton X-100). For EdU detection, the fixed and permeabilized cells were processed as instructed by the manufacturer's protocol (Invitrogen; Click-it EdU Alexa Fluor 488 Imaging Kit; Cat # C10337) and afterwards DAPI stained and mounted using ProLong Gold antifade reagent with DAPI (life technologies). The cells were later on imaged by confocal microscopy. As shown in FIGS. 11A-11D, the exosomal DNA is able to enter the cytoplasm and nucleus of both the mouse bone marrow cells and the RAW 264.7 cells.

Discussion of Examples 1-6

Exosomes are important mediators of communication between tumor cells and the cells in their surrounding microenvironment, both locally and distally. Thus, the composition of exosomes derived from cancer cells can influence the adhesion, fusion and transfer to recipient cells. Here, it is demonstrated that dsDNA predominates as the primary nucleic acid structure present in exosomes derived from cancer cells. Moreover, it was found that the entire genome was represented in exosomes and that the mutations present in the parental tumor cells can be readily identified in exosomes. These findings have significant translational implications for diagnostic and therapeutic monitoring of patients with cancer. Currently, there is a high level of interest in the potential of circulating nucleic acids and circulating tumor cells (CTCs) in patient serum to serve as markers for detection and monitoring of cancer (Waldenstrom et al., "Cardiomyocyte Microvesicles Contain DNA/RNA and Convey Biological Messages to Target Cells," *PloS One* 7:e34653 (2012), which is hereby incorporated by reference in its entirety). However, progress in this area has been hindered by limitations in the sensitivity of these assays, as CTCs are extremely rare, and free, circulating DNA can easily be degraded. However, the dsDNA inside the exosomes is protected from extracellular nucleases and thus can represent a more reliable and stable source of tumor DNA that can be assayed for mutations. The inherent stability of dsDNA in exosomes may also be the basis for a functional role of exoDNA in intercellular genetic communication. Understanding the mechanism of dsDNA transfer and integration in recipient cells will lead to a better understanding of the role of tumor exosomes in cancer and metastasis.

Interestingly, the EM study provides the first direct evidence that only a subset of exosomes contain DNA. This finding raises the question of whether DNA packaging into exosomes is randomly restricted to a subset of particles due to size and distribution limitations, or whether there are specific biogenesis mechanisms that allow DNA packaging specifically in this particular subset of exosomes. It is possible that heterogeneous populations of exosome particles are present in the cancer microenvironment and the content of exosomes indirectly reflects the status of the cancer cells. Since exosomes are cellular in origin, the biomolecular composition of exosomes may further reflect cellular compartment of its origin.

Noteworthy, exoDNA is present in exosomes derived from most tumors, but not all tumor types, such as pancreatic cancer. Therefore, education of recipient cells via exosomes may depend on the genetic makeup of the uptaken exosomes. For example, the education of BMDC in the metastatic environment can involve both epigenetic and genetic processes. While the presence of ssDNA and non-coding RNAs explains the process of epigenetic education, presence of dsDNA may be associated with more permanent genetic changes. For example, the ability of dsDNA to undergo homologous recombination may account for the exosome-mediated transfer of genetic lesions to cells in the distant metastatic organs during cancer progression.

In this study, a thorough characterization of the nature, size and distribution pattern of DNA associated with exosomes was performed by using ssDNA and dsDNA specific enzymes on the intact exosomes. Interestingly, the exoDNA associated with the exterior of the exosome is larger in size in comparison to the exoDNA actually packaged into the exosome, which ranges between 100 bp to 2500 bp. Therefore, investigations in external and internal exoDNA are ongoing and may possibly have distinct functional roles in cancer progression.

While CTCs are extremely rare and their isolation requires specialized procedures, exosomes are constitutively secreted by all tumor cells, abundant in the plasma of metastatic cancer patients (Peinado et al., "Melanoma Exosomes Educate Bone Marrow Progenitor Cells Toward a Pro-metastatic Phenotype Through MET," *Nature Medicine* 18:883-891 (2012), which is hereby incorporated by reference in its entirety), and their isolation requires no special equipment. Therefore, an exoDNA-based test may be feasible in standard laboratories. Since aberrant DNA methylation patterns have been associated with certain types of cancer and its progression, it is reasonable to expect that exoDNA can be used as a surrogate for tumor cells to examine the relevant cancer-associated epigenetic alterations. It is also possible that the mutational status of a primary tumor can vary from that of the metastatic sites, and that mutations detected in exosomal DNA isolated from the plasma of cancer patients may not necessarily represent the mutational status of the primary tumor. This would suggest that targeted therapy to specific mutations may have a role in select patients whose primary tumors which lack a specific mutation, which may instead, be revealed in plasma-derived exosomes of cancer patients. In conclusion, it has been demonstrated herein that double-stranded exoDNA has unique features and value for the development of diagnostic/prognostic tools.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed is:

1. A method of prognosing cancer in a subject, said method comprising:
   selecting a subject having cancer;
   obtaining, from the selected subject, a sample containing exosomes;
   recovering the exosomes from the sample;
   removing DNA from outside of the recovered exosomes;
   isolating double-stranded DNA, a majority of which has a size of less than 2500 bp, from within said exosomes after said removing;
   contacting the isolated double-stranded DNA with one or more reagents suitable to: (1) detect the presence or absence of one or more genetic mutations in the isolated double-stranded DNA that are associated with cancer, (2) quantify the amount of isolated double-stranded DNA from the recovered exosomes in the sample, or (3) detect the methylation status of the isolated double-stranded DNA;
   determining a difference between (1) the presence or absence of one or more genetic mutations in the isolated double-stranded DNA that are associated with cancer and a reference sample, (2) the quantified amount of isolated double-stranded DNA from the recovered exosomes in the sample and a reference sample, or (3) the methylation status of the isolated double-stranded DNA and a reference sample; and
   prognosing the cancer based on said determining, wherein a difference in the presence or absence of one or more genetic mutations in the isolated double-stranded DNA, the quantified amount of isolated double-stranded DNA from the recovered exosomes, or the methylation status of the isolated double-stranded DNA relative to the reference sample prognoses the cancer.

2. The method of claim 1, wherein said sample is blood.

3. The method of claim 1, wherein said contacting is carried out by detecting the presence or absence of one or more genetic mutations in the isolated double-stranded DNA that are associated with cancer.

4. The method of claim 1, wherein said contacting is suitable for quantifying the amount of isolated double-stranded DNA from the recovered exosomes in the sample.

5. The method of claim 4, wherein said quantifying is carried out by comparing the amount of isolated double-stranded DNA to that in a prior sample obtained from the selected subject and subjected to said recovering, said isolating, and said contacting.

6. The method of claim 4, wherein said quantifying is carried out by comparing the amount of isolated double-stranded DNA to a standard.

7. The method of claim 1, wherein said contacting is suitable for detecting the methylation status of the isolated double-stranded DNA.

8. The method of claim 1, wherein said prognosing is carried out to predict sites of metastasis, to determine the stage of the cancer, or to identify the location of a primary tumor in the subject.

9. The method of claim 1 further comprising:
   selecting a suitable cancer therapeutic based on said prognosing and
   administering the selected cancer therapeutic to said selected subject.

10. The method of claim 1, wherein the cancer is selected from the group consisting of melanoma, breast cancer, lung cancer, and leukemia.

11. The method of claim 1, wherein said prognosing is carried out to predict the metastatic potential of the cancer.

12. The method of claim 1, wherein said one or more reagents suitable for detecting the presence or absence of one or more mutations in the sample are suitable for carrying out allele-specific polymerase chain reaction (PCR) or genomic sequencing.

13. The method of claim 3, wherein the selected subject has melanoma and the presence or absence of a mutation in BRAF is detected.

14. The method of claim 3, wherein the presence or absence of one or more mutations in EGFR is detected.

15. The method of claim 14, wherein the one or more mutations in EGFR is selected from the group consisting of an exon 19 deletion, L858R, T790M, and any combination thereof.

16. The method of claim 3, wherein said one or more genetic mutations are mutations in genes selected from the group consisting of BRA, EGFR, APC, NOTCH1, HRAS, KRAS, NRAS, MET, p53, PTEN, HER2, FLT3, BRCA1, BRCA2, PIK3CA, KIT, RET, AKT, ABL, CDK4, MYC, RAF, PDGFR, BCR-ABL, NPM1, CEBPalpha, and SRC.

17. The method of claim 8, wherein said prognosing is carried out to predict sites of metastasis.

18. The method of claim 8, wherein said prognosing is carried out to determine the stage of the cancer.

19. The method of claim 8, wherein said prognosing is carried out to identify the location of a primary tumor in the subject.

20. The method of claim 1, wherein the isolated double-stranded has a size range of 100 bp to 2500 bp.

21. A method comprising:
    selecting a subject having cancer;
    obtaining, from the selected subject, a sample containing exosomes;
    recovering the exosomes from the sample;
    removing DNA from outside of the recovered exosomes;
    isolating double-stranded DNA, a majority of which has a size of less than 2500 bp, from within said exosomes after said removing; and
    contacting the isolated double-stranded DNA with one or more reagents suitable to: (1) detect the presence or absence of one or more genetic mutations in the isolated double-stranded DNA that are associated with cancer, (2) quantify the amount of isolated double-stranded DNA from the recovered exosomes in the sample, or (3) detect the methylation status of the isolated double-stranded DNA.

22. The method of claim 21 further comprising:
    determining a difference between (1) the presence or absence of one or more genetic mutations in the isolated double-stranded DNA that are associated with cancer and a reference sample, (2) the quantified amount of isolated double-stranded DNA from the recovered exosomes in the sample and a reference sample, or (3) the methylation status of the isolated double-stranded DNA and a reference sample after said contacting.

23. The method of claim 21, wherein said sample is blood.

24. The method of claim 21, wherein said one or more reagents suitable for detecting the presence or absence of one or more mutations in the sample are suitable for carrying out allele-specific polymerase chain reaction (PCR) or genomic sequencing.

* * * * *

SEQUENCE LISTING

```
<160> NUMBER OF SEQ ID NOS: 4

<210> SEQ ID NO 1
<211> LENGTH: 766
<212> TYPE: PRT
<213> ORGANISM: Homo sapiens

<400> SEQUENCE: 1

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
```

-continued

```
            115                 120                 125
Ser Val Leu Pro Ser Ser Leu Ser Val Phe Gln Asn Pro Thr Asp Val
        130                 135                 140
Ala Arg Ser Asn Pro Lys Ser Pro Gln Lys Pro Ile Val Arg Val Phe
145                 150                 155                 160
Leu Pro Asn Lys Gln Arg Thr Val Val Pro Ala Arg Cys Gly Val Thr
                165                 170                 175
Val Arg Asp Ser Leu Lys Lys Ala Leu Met Met Arg Gly Leu Ile Pro
            180                 185                 190
Glu Cys Cys Ala Val Tyr Arg Ile Gln Asp Gly Glu Lys Lys Pro Ile
                195                 200                 205
Gly Trp Asp Thr Asp Ile Ser Trp Leu Thr Gly Glu Glu Leu His Val
            210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
                245                 250                 255
Gln Gly Phe Arg Cys Gln Thr Cys Gly Tyr Lys Phe His Gln Arg Cys
                260                 265                 270
Ser Thr Glu Val Pro Leu Met Cys Val Asn Tyr Asp Gln Leu Asp Leu
            275                 280                 285
Leu Phe Val Ser Lys Phe Phe Glu His His Pro Ile Pro Gln Glu Glu
            290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
                325                 330                 335
Ser Lys Ser Ile Pro Ile Pro Gln Pro Phe Arg Pro Ala Asp Glu Asp
                340                 345                 350
His Arg Asn Gln Phe Gly Gln Arg Asp Arg Ser Ser Ser Ala Pro Asn
                355                 360                 365
Val His Ile Asn Thr Ile Glu Pro Val Asn Ile Asp Asp Leu Ile Arg
            370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
                405                 410                 415
Gln Lys Ser Pro Gly Pro Gln Arg Glu Arg Lys Ser Ser Ser Ser Ser
                420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
            450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
                500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
            530                 535                 540
```

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Val Lys Ser Arg Trp Ser Gly Ser His
    595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670

Tyr Leu Ser Pro Asp Leu Ser Lys Val Arg Ser Asn Cys Pro Lys Ala
    675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
        740                 745                 750

Thr Pro Ile Gln Ala Gly Gly Tyr Gly Ala Phe Pro Val His
    755                 760                 765

<210> SEQ ID NO 2
<211> LENGTH: 2949
<212> TYPE: DNA
<213> ORGANISM: Homo sapiens

<400> SEQUENCE: 2
cgcctccctt ccccctcccc gcccgacagc ggccgctcgg gccccggctc tcggttataa    60
gatggcggcg ctgagcggtg gcggtggtgg cggcgcggag ccgggccagg ctctgttcaa   120
cggggacatg gagcccgagg ccggcgccgg cgccggcgcc gcggcctctt cggctgcgga   180
ccctgccatt ccgaggaggt gtggaatat caaacaaatg attaagttga cacaggaaca   240
tatagaggcc ctattggaca aatttggtgg ggagcataat ccaccatcaa tatatctgga   300
ggcctatgaa gaatacacca gcaagctaga tgcactccaa caaagagaac aacagttatt   360
ggaatctctg gggaacggaa ctgatttttc tgtttctagc tctgcatcaa tggataccgt   420
tacatcttct tcctcttcta gcctttcagt gctaccttca tctctttcag ttttttcaaaa   480
tcccacagat gtggcacgga gcaaccccaa gtcaccacaa aaacctatcg ttagagtctt   540
cctgcccaac aaacagagga cagtggtacc tgcaaggtgt ggagttacag tccgagacag   600
tctaaagaaa gcactgatga tgagaggtct aatcccagag tgctgtgctg tttacagaat   660
tcaggatgga gagaagaaac caattggttg ggacactgat atttcctggc ttactggaga   720
agaattgcat gtggaagtgt tggagaatgt tccacttaca acacacaact ttgtacgaaa   780
aacgtttttc accttagcat tttgtgactt ttgtcgaaag ctgcttttcc agggtttccg   840

| | |
|---|---|
| ctgtcaaaca tgtggttata aatttcacca gcgttgtagt acagaagttc cactgatgtg | 900 |
| tgttaattat gaccaacttg atttgctgtt tgtctccaag ttctttgaac accacccaat | 960 |
| accacaggaa gaggcgtcct tagcagagac tgccctaaca tctggatcat ccccttccgc | 1020 |
| acccgcctcg gactctattg gccccaaat tctcaccagt ccgtctcctt caaaatccat | 1080 |
| tccaattcca cagcccttcc gaccagcaga tgaagatcat cgaaatcaat ttgggcaacg | 1140 |
| agaccgatcc tcatcagctc caatgtgca tataaacaca atagaacctg tcaatattga | 1200 |
| tgacttgatt agagaccaag gatttcgtgg tgatggagga tcaaccacag gtttgtctgc | 1260 |
| tacccccct gcctcattac ctggctcact aactaacgtg aaagccttac agaaatctcc | 1320 |
| aggacctcag cgagaaagga agtcatcttc atcctcagaa acaggaatc gaatgaaaac | 1380 |
| acttggtaga cgggactcga gtgatgattg ggagattcct gatgggcaga ttacagtggg | 1440 |
| acaaagaatt ggatctggat catttggaac agtctacaag ggaaagtggc atggtgatgt | 1500 |
| ggcagtgaaa atgttgaatg tgacagcacc tacacctcag cagttacaag ccttcaaaaa | 1560 |
| tgaagtagga gtactcagga aaacacgaca tgtgaatatc ctactcttca tgggctattc | 1620 |
| cacaaagcca caactggcta ttgttaccca gtggtgtgag ggctccagct tgtatcacca | 1680 |
| tctccatatc attgagacca aatttgagat gatcaaactt atagatattg cacgacagac | 1740 |
| tgcacagggc atggattact tacacgccaa gtcaatcatc cacagagacc tcaagagtaa | 1800 |
| taatatattt cttcatgaag acctcacagt aaaaataggt gattttggtc tagctacagt | 1860 |
| gaaatctcga tggagtgggt cccatcagtt tgaacagttg tctggatcca ttttgtggat | 1920 |
| ggcaccagaa gtcatcagaa tgcaagataa aaatccatac agctttcagt cagatgtata | 1980 |
| tgcatttgga attgttctgt atgaattgat gactggacag ttaccttatt caaacatcaa | 2040 |
| caacagggac cagataattt ttatggtggg acgaggatac ctgtctccag atctcagtaa | 2100 |
| ggtacggagt aactgtccaa aagccatgaa gagattaatg gcagagtgcc tcaaaaagaa | 2160 |
| aagagatgag agaccactct ttcccccaaat tctcgcctct attgagctgc tggcccgctc | 2220 |
| attgccaaaa attcaccgca gtgcatcaga accctccttg aatcgggctg gtttccaaac | 2280 |
| agaggatttt agtctatatg cttgtgcttc tccaaaaaca cccatccagg caggggata | 2340 |
| tggtgcgttt cctgtccact gaaacaaatg agtgagagag ttcaggagag tagcaacaaa | 2400 |
| aggaaaataa atgaacatat gtttgcttat atgttaaatt gaataaaata ctctcttttt | 2460 |
| ttttaaggtg aaccaaagaa cacttgtgtg gttaaagact agatataatt tttccccaaa | 2520 |
| ctaaaattta tacttaacat tggattttta acatccaagg gttaaaatac atagacattg | 2580 |
| ctaaaaattg gcagagcctc ttctagaggc tttactttct gttccgggtt tgtatcattc | 2640 |
| acttggttat tttaagtagt aaacttcagt ttctcatgca acttttgttg ccagctatca | 2700 |
| catgtccact agggactcca gaagaagacc ctacctatgc ctgtgtttgc aggtgagaag | 2760 |
| ttggcagtcg gttagcctgg gttagataag gcaaactgaa cagatctaat ttaggaagtc | 2820 |
| agtagaattt aataattcta ttattattct taataatttt tctataacta tttcttttta | 2880 |
| taacaatttg gaaatgtgg atgtctttta tttccttgaa gcaataaact aagtttcttt | 2940 |
| ttataaaaa | 2949 |

<210> SEQ ID NO 3
<211> LENGTH: 1209
<212> TYPE: PRT
<213> ORGANISM: Homo sapiens

<400> SEQUENCE: 3

```
Arg Pro Ser Gly Thr Ala Gly Ala Ala Leu Leu Ala Leu Leu Ala Ala
1               5                   10                  15

Leu Cys Pro Ala Ser Arg Ala Leu Glu Lys Lys Val Cys Gln Gly
            20                  25                  30

Thr Ser Asn Lys Leu Thr Gln Leu Gly Thr Phe Glu Asp His Phe Leu
        35                  40                  45

Ser Leu Gln Arg Met Phe Asn Asn Cys Glu Val Val Leu Gly Asn Leu
50                  55                  60

Glu Ile Thr Tyr Val Gln Arg Asn Tyr Asp Leu Ser Phe Leu Lys Thr
65                  70                  75                  80

Ile Gln Glu Val Ala Gly Tyr Val Leu Ile Ala Leu Asn Thr Val Glu
                85                  90                  95

Arg Ile Pro Leu Glu Asn Leu Gln Ile Ile Arg Gly Asn Met Tyr Tyr
                100                 105                 110

Glu Asn Ser Tyr Ala Leu Ala Val Leu Ser Asn Tyr Asp Ala Asn Lys
            115                 120                 125

Thr Gly Leu Lys Glu Leu Pro Met Arg Asn Leu Gln Glu Ile Leu His
        130                 135                 140

Gly Ala Val Arg Phe Ser Asn Asn Pro Ala Leu Cys Asn Val Glu Ser
145                 150                 155                 160

Ile Gln Trp Arg Asp Ile Val Ser Ser Asp Phe Leu Ser Asn Met Ser
                165                 170                 175

Met Asp Phe Gln Asn His Leu Gly Ser Cys Gln Lys Cys Asp Pro Ser
            180                 185                 190

Cys Pro Asn Gly Ser Cys Trp Gly Ala Gly Glu Glu Asn Cys Gln Lys
        195                 200                 205

Leu Thr Lys Ile Ile Cys Ala Gln Gln Cys Ser Gly Arg Cys Arg Gly
210                 215                 220

Lys Ser Pro Ser Asp Cys Cys His Asn Gln Cys Ala Ala Gly Cys Thr
225                 230                 235                 240

Gly Pro Arg Glu Ser Asp Cys Leu Val Cys Arg Lys Phe Arg Asp Glu
                245                 250                 255

Ala Thr Cys Lys Asp Thr Cys Pro Pro Leu Met Leu Tyr Asn Pro Thr
            260                 265                 270

Thr Tyr Gln Met Asp Val Asn Pro Glu Gly Lys Tyr Ser Phe Gly Ala
        275                 280                 285

Thr Cys Val Lys Lys Cys Pro Arg Asn Tyr Val Val Thr Asp His Gly
    290                 295                 300

Ser Cys Val Arg Ala Cys Gly Ala Asp Ser Tyr Glu Met Glu Glu Asp
305                 310                 315                 320

Gly Val Arg Lys Cys Lys Lys Cys Glu Gly Pro Cys Arg Lys Val Cys
                325                 330                 335

Asn Gly Ile Gly Ile Gly Glu Phe Lys Asp Ser Leu Ser Ile Asn Ala
            340                 345                 350

Thr Asn Ile Lys His Phe Lys Asn Cys Thr Ser Ile Ser Gly Asp Leu
        355                 360                 365

His Ile Leu Pro Val Ala Phe Arg Gly Asp Ser Phe Thr His Thr Pro
    370                 375                 380

Pro Leu Asp Pro Gln Glu Leu Asp Ile Leu Lys Thr Val Lys Glu Ile
385                 390                 395                 400

Thr Gly Phe Leu Leu Ile Gln Ala Trp Pro Glu Asn Arg Thr Asp Leu
                405                 410                 415
```

-continued

```
His Ala Phe Glu Asn Leu Glu Ile Ile Arg Gly Arg Thr Lys Gln His
                420                 425                 430

Gly Gln Phe Ser Leu Ala Val Val Ser Leu Asn Ile Thr Ser Leu Gly
            435                 440                 445

Leu Arg Ser Leu Lys Glu Ile Ser Asp Gly Asp Val Ile Ile Ser Gly
        450                 455                 460

Asn Lys Asn Leu Cys Tyr Ala Asn Thr Ile Asn Trp Lys Lys Leu Phe
465                 470                 475                 480

Gly Thr Ser Gly Gln Lys Thr Lys Ile Ile Ser Asn Arg Gly Glu Asn
                485                 490                 495

Ser Cys Lys Ala Thr Gly Gln Val Cys His Ala Leu Cys Ser Pro Glu
            500                 505                 510

Gly Cys Trp Gly Pro Glu Pro Arg Asp Cys Val Ser Cys Arg Asn Val
        515                 520                 525

Ser Arg Gly Arg Glu Cys Val Asp Lys Cys Asn Leu Leu Glu Gly Glu
    530                 535                 540

Pro Arg Glu Phe Val Glu Asn Ser Glu Cys Ile Gln Cys His Pro Glu
545                 550                 555                 560

Cys Leu Pro Gln Ala Met Asn Ile Thr Cys Thr Gly Arg Gly Pro Asp
                565                 570                 575

Asn Cys Ile Gln Cys Ala His Tyr Ile Asp Gly Pro His Cys Val Lys
            580                 585                 590

Thr Cys Pro Ala Gly Val Met Gly Glu Asn Asn Thr Leu Val Trp Lys
        595                 600                 605

Tyr Ala Asp Ala Gly His Val Cys His Leu Cys His Pro Asn Cys Thr
    610                 615                 620

Tyr Gly Cys Thr Gly Pro Gly Leu Glu Gly Cys Pro Thr Asn Gly Pro
625                 630                 635                 640

Lys Ile Pro Ser Ile Ala Thr Gly Met Val Gly Ala Leu Leu Leu Leu
                645                 650                 655

Leu Val Val Ala Leu Gly Ile Gly Leu Phe Met Arg Arg Arg His Ile
            660                 665                 670

Val Arg Lys Arg Thr Leu Arg Arg Leu Leu Gln Glu Arg Glu Leu Val
        675                 680                 685

Glu Pro Leu Thr Pro Ser Gly Glu Ala Pro Asn Gln Ala Leu Leu Arg
    690                 695                 700

Ile Leu Lys Glu Thr Glu Phe Lys Lys Ile Lys Val Leu Gly Ser Gly
705                 710                 715                 720

Ala Phe Gly Thr Val Tyr Lys Gly Leu Trp Ile Pro Glu Gly Glu Lys
                725                 730                 735

Val Lys Ile Pro Val Ala Ile Lys Glu Leu Arg Glu Ala Thr Ser Pro
            740                 745                 750

Lys Ala Asn Lys Glu Ile Leu Asp Glu Ala Tyr Val Met Ala Ser Val
        755                 760                 765

Asp Asn Pro His Val Cys Arg Leu Leu Gly Ile Cys Leu Thr Ser Thr
    770                 775                 780

Val Gln Leu Ile Thr Gln Leu Met Pro Phe Gly Cys Leu Leu Asp Tyr
785                 790                 795                 800

Val Arg Glu His Lys Asp Asn Ile Gly Ser Gln Tyr Leu Leu Asn Trp
                805                 810                 815

Cys Val Gln Ile Ala Lys Gly Met Asn Tyr Leu Glu Asp Arg Arg Leu
            820                 825                 830

Val His Arg Asp Leu Ala Ala Arg Asn Val Leu Val Lys Thr Pro Gln
```

835                 840                 845
His Val Lys Ile Thr Asp Phe Gly Leu Ala Lys Leu Leu Gly Ala Glu
            850                 855                 860

Glu Lys Glu Tyr His Ala Gly Gly Lys Val Pro Ile Lys Trp Met
865                 870                 875                 880

Ala Leu Glu Ser Ile Leu His Arg Ile Tyr Thr His Gln Ser Asp Val
                885                 890                 895

Trp Ser Tyr Gly Val Thr Val Trp Glu Leu Met Thr Phe Gly Ser Lys
            900                 905                 910

Pro Tyr Asp Gly Ile Pro Ala Ser Glu Ile Ser Ser Ile Leu Glu Lys
            915                 920                 925

Gly Glu Arg Leu Pro Gln Pro Pro Ile Cys Thr Ile Asp Val Tyr Met
            930                 935                 940

Ile Met Val Lys Cys Trp Met Ile Asp Ala Asp Ser Arg Pro Lys Phe
945                 950                 955                 960

Arg Glu Leu Ile Ile Glu Phe Ser Lys Met Ala Arg Asp Pro Gln Arg
                965                 970                 975

Tyr Leu Val Ile Gln Gly Asp Glu Arg Met His Leu Pro Ser Pro Thr
            980                 985                 990

Asp Ser Asn Phe Tyr Arg Ala Leu Met Asp Glu Glu Asp Met Asp Asp
            995                1000                1005

Val Val Asp Ala Asp Glu Tyr Leu Ile Pro Gln Gln Gly Phe Phe
     1010                1015                1020

Ser Ser Pro Ser Thr Ser Arg Thr Pro Leu Leu Ser Ser Leu Ser
     1025                1030                1035

Ala Thr Ser Asn Asn Ser Thr Val Ala Cys Ile Asp Arg Asn Gly
     1040                1045                1050

Leu Gln Ser Cys Pro Ile Lys Glu Asp Ser Phe Leu Gln Arg Tyr
     1055                1060                1065

Ser Ser Asp Pro Thr Gly Ala Leu Thr Glu Asp Ser Ile Asp Asp
     1070                1075                1080

Thr Phe Leu Pro Val Pro Glu Tyr Ile Asn Gln Ser Val Pro Lys
     1085                1090                1095

Arg Pro Ala Gly Ser Val Gln Asn Pro Val Tyr His Asn Gln Pro
     1100                1105                1110

Leu Asn Pro Ala Pro Ser Arg Asp Pro His Tyr Gln Asp Pro His
     1115                1120                1125

Ser Thr Ala Val Gly Asn Pro Glu Tyr Leu Asn Thr Val Gln Pro
     1130                1135                1140

Thr Cys Val Asn Ser Thr Phe Asp Ser Pro Ala His Trp Ala Gln
     1145                1150                1155

Lys Gly Ser His Gln Ile Ser Leu Asp Asn Pro Asp Tyr Gln Gln
     1160                1165                1170

Asp Phe Phe Pro Lys Glu Ala Lys Pro Asn Gly Ile Phe Lys Gly
     1175                1180                1185

Ser Thr Ala Glu Asn Ala Glu Tyr Leu Arg Val Ala Pro Gln Ser
     1190                1195                1200

Ser Glu Phe Ile Gly Ala
     1205

<210> SEQ ID NO 4
<211> LENGTH: 5616
<212> TYPE: DNA
<213> ORGANISM: Homo sapiens

<400> SEQUENCE: 4

```
ccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcgatgc gaccctccgg gacggccggg gcagcgctcc tggcgctgct ggctgcgctc     300
tgcccggcga gtcgggctct ggaggaaaag aaagtttgcc aaggcacgag taacaagctc     360
acgcagttgg gcacttttga agatcatttt ctcagcctcc agaggatgtt caataactgt     420
gaggtggtcc ttgggaattt ggaaattacc tatgtgcaga ggaattatga tctttccttc     480
ttaaagacca tccaggaggt ggctggttat gtcctcattg ccctcaacac agtggagcga     540
attcctttgg aaaacctgca gatcatcaga ggaaatatgt actacgaaaa ttcctatgcc     600
ttagcagtct tatctaacta tgatgcaaat aaaaccggac tgaaggagct gcccatgaga     660
aatttacagg aaatcctgca tggcgccgtg cggttcagca caaccctgcc ctgtgcaac      720
gtggagagca tccagtggcg ggacatagtc agcagtgact ttctcagcaa catgtcgatg     780
gacttccaga accacctggg cagctgccaa aagtgtgatc caagctgtcc caatgggagc     840
tgctggggtg caggagagga gaactgccag aaactgacca aaatcatctg tgcccagcag     900
tgctccgggc gctgccgtgg caagtccccc agtgactgct gccacaacca gtgtgctgca     960
ggctgcacag gccccggga gcgactgc ctggtctgcc gcaaattccg agacgaagcc    1020
acgtgcaagg acacctgccc cccactcatg ctctacaacc ccaccacgta ccagatggat    1080
gtgaaccccg agggcaaata cagctttggt gccacctgcg tgaagaagtg tccccgtaat    1140
tatgtggtga cagatcacgg ctcgtgcgtc cgagcctgtg gggccgacag ctatgagatg    1200
gaggaagacg gcgtccgcaa gtgtaagaag tgcgaagggc cttgccgcaa agtgtgtaac    1260
ggaataggta ttggtgaatt taaagactca ctctccataa atgctacgaa tattaaacac    1320
ttcaaaaact gcacctccat cagtggcgat ctccacatcc tgccggtggc atttagggt     1380
gactccttca cacatactcc tcctctggat ccacaggaac tggatattct gaaaaccgta    1440
aaggaaatca cagggttttt gctgattcag gcttggcctg aaaacaggac ggacctccat    1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag caggaatg cgtggacaag    1860
tgcaaccttc tggagggtga gccaagggag tttgtggaga actctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag gtcttgaagg ctgtccaacg    2160
aatgggccta agatcccgtc catcgccact gggatggtgg gggccctcct cttgctgctg    2220
gtggtggccc tggggatcgg cctcttcatg cgaaggcgcc acatcgttcg gaagcgcacg    2280
```

```
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc ccacgtgtg ccgcctgctg     2580 ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatcctctc catcctggag aaaggagaaa gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatgaa agaatgcat ttgccaagtc ctacagactc caacttctac      3240
cgtgccctga tggatgaaga agacatggac gacgtggtgg atgccgacga gtacctcatc    3300
ccacagcagg gcttcttcag cagcccctcc acgtcacgga ctccccttcct gagctctctg    3360 agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttcttcccc    3780
aaggaagcca agccaaatgg catctttaag ggctccacag ctgaaaatgc agaatacctca    3840 agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt cccttttgagc agaaatttat   4140 ctttcaaaga ggtatatttg aaaaaaaaaa aaagtatatg tgaggatttt tattgattgg    4200
ggatcttgga gttttttcatt gtcgctattg atttttactt caatgggctc ttccaacaag   4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
```

```
caagagagga tgacacatca aataataact cggattccag cccacattgg attcatcagc    4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920 acccccaaa attagtttgt gttacttatg gaagatagtt ttctccttt acttcacttc     4980 aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220 agatgttta gaaggaaaaa agttccttcc taaaataatt tctctacaat tggaagattg    5280
gaagattcag ctagttagga gcccacctt tttcctaatc tgtgtgtgcc ctgtaacctg     5340
actggttaac agcagtcctt tgtaaacagt gttttaaact ctcctagtca atatccaccc    5400
catccaattt atcaaggaag aaatggttca gaaaatattt tcagcctaca gttatgttca    5460
gtcacacaca catacaaaat gttccttttg cttttaaagt aattttgac tcccagatca     5520 gtcagagccc ctacagcatt gttaagaaag tatttgattt ttgtctcaat gaaaataaaa    5580
ctatattcat ttccactcta aaaaaaaaaa aaaaaa                              5616
```